US011944655B2

(12) United States Patent
Klotz Ceberio et al.

(10) Patent No.: US 11,944,655 B2
(45) Date of Patent: Apr. 2, 2024

(54) PROBIOTIC MICROCAPSULE

(71) Applicant: ALPINA PRODUCTOS ALIMENTICIOS S.A., Sopó (CO)

(72) Inventors: Bernadette Francisca Klotz Ceberio, Bogotá (CO); Maria Ximena Quintanilla Carvajal, Bogotá (CO)

(73) Assignee: Alpina Productos Alimenticios, S.A., Sopó (CO)

(*) Notice: Subject to any disclaimer, the term of this patent is extended or adjusted under 35 U.S.C. 154(b) by 411 days.

(21) Appl. No.: 17/039,859

(22) Filed: Sep. 30, 2020

(65) Prior Publication Data

US 2021/0113629 A1    Apr. 22, 2021

(30) Foreign Application Priority Data

Oct. 22, 2019   (CO) .................. NC2019/0011687

(51) Int. Cl.
*A61K 35/742*  (2015.01)
*A61K 9/50*    (2006.01)

(52) U.S. Cl.
CPC .......... *A61K 35/742* (2013.01); *A61K 9/5015* (2013.01); *A61K 9/5036* (2013.01); *A61K 9/5052* (2013.01); *A61K 9/5057* (2013.01); *A61K 9/5063* (2013.01)

(58) Field of Classification Search
CPC .. A61K 35/742; A61K 9/5015; A61K 9/5036; A61K 9/5052; A61K 9/5057; A61K 9/5063; A61K 35/741; A23L 2/52; A23L 29/212; A23L 29/30; A23L 33/115; A23L 33/125; A23L 33/135; A23L 33/17; A23P 10/30; A23P 10/35; A23P 20/105
See application file for complete search history.

(56) References Cited

U.S. PATENT DOCUMENTS

| | | | |
|---|---|---|---|
| 8,871,266 | B2 | 10/2014 | Crittenden et al. |
| 10,143,649 | B2 | 12/2018 | Lefkowitz |
| 2007/0042184 | A1 | 2/2007 | Coyne et al. |
| 2007/0098847 | A1 | 5/2007 | Teissier |
| 2007/0122397 | A1 | 5/2007 | Sanguansri et al. |
| 2011/0189298 | A1 | 8/2011 | Vos et al. |
| 2019/0133941 | A1* | 5/2019 | Mody ............... A61P 1/14 |
| 2019/0254302 | A1 | 8/2019 | Abbaspourrad et al. |

FOREIGN PATENT DOCUMENTS

| | | | | |
|---|---|---|---|---|
| CN | 104435283 | A | * 3/2015 | ........... A61K 31/702 |
| WO | 2005070221 | A1 | 8/2005 | |

OTHER PUBLICATIONS

Kleeman et al. Food Hydrocolloids 83 (2018) 365-374. (Year: 2018).*

Rosenberg et al. Appl. Sci. Aug. 2018, 1944. (Year: 2018).*

Filippidi et al. Adv. Funct. Mater. 2014, 24, 5962-5968. (Year: 2014).*

Maathuis A.J.H, Keller D., Farmer S., "Survival and metabolic activity of the GanedenBC30 strain of Bacillus coagulans in a dynamic in vitro model of the stomach and small intestine", Beneficial Microbes, 2010; pp. 31-36, vol. 1 No. (1), Wageningen Academic Publishers, The Netherlands.

Corona-Hernández Rocío I., Álvarez-Parrilla Emilio, Lizardi-Mendoza Jaime, Islas-Rubio Alma R., De La Rosa Laura. A., Wall-Medrano Abraham, "Structural Stability and Viability of Microencapsulated Probiotic Bacteria: A Review", Comprehensive Reviews in Food Science and Food Safety, 2013, pp. 616-628, vol. 12, Institute of Food Technologists, Mexico.

Chávarri María, Marañón Izaskun, Villarán María Carmen, "Encapsulation Technology to Protect Probiotic Bacteria", ResearchGate, 2012, pp. 501-540, IntechOpen Limited, Spain.

Das Arpita, Ray Sohini, Raychaudhuri Utpal, Chakraborty Runu,"Microencapsulation of Probiotic Bacteria and its Potential Application in Food Technology", International Journal of Agriculture, Environment & Biotechnology, Mar. 2014, pp. 63-69, vol. 6 No. (1), New Delhi Publishers, New Delhi, India.

Corrêa-Filho Luiz C., Moldão-Martins Margarida, Alves Vitor D., "Advances in the Application of Microcapsules as Carriers of Functional Compounds for Food Products", Applied Sciences, Feb. 2019, pp. 571-535, vol. 9 No. (3), MDPI, Basel, Switzerland.

Terpou Antonia, Papadaki Aikaterini, Lappa Iliada K., Kachrimanidou Vasiliki, Bosnea Loulouda A., Kopsahelis Nikolaos, "Probiotics in Food Systems: Significance and Emerging Strategies Towards Improved Viability and Delivery of Enhanced Beneficial Value", Nutrients, Jul. 2019, pp. 1591-1623, vol. 11 No. (7), MDPI, Basel, Switzerland.

Matos-Jr Fernando Eustáquio, Di Sabatino Marcello, Passerini Nadia, Favaro-Trindade Carmen Sílvia, Albertini Beatrice, "Development and characterization of solid lipid microparticles loaded with ascorbic acid and produced by spray congealing", Food Research International, 2015, pp. 52-59, vol. 67, Canada.

Gavory Cécile, Abderrahmen Robin, Bordes Claire, Chaussy Didier, Naceur Belgacem Mohamed, Fessi Hatem, Briancon Stéphanie, "Encapsulation of a pressure sensitive adhesive by spray-cooling: Optimum formulation and processing conditions", Advanced Powder Technology, 2014, pp. 292-300, vol. 25 No. (1), Japan.

(Continued)

*Primary Examiner* — Mina Haghighatian
*Assistant Examiner* — Janice Y Silverman
(74) *Attorney, Agent, or Firm* — The Morales Law Firm; Joseph L. Morales, Esq.

(57) ABSTRACT

The invention is directed to a microcapsule and the method to obtain it. The microcapsule comprises a core in the form of a lipid sphere coated by a protein film, wherein the lipid sphere comprises sporulated microorganisms and at least one lipid wall material, and the protein film is a mix of carbohydrate, protein material and water. The method to obtain this microcapsule includes the stages of mixing sphere components, mixing protein film components, homogenizing the protein film and the subsequent coating of the lipid sphere by means of fluidization with the protein film.

15 Claims, 22 Drawing Sheets

(56) References Cited

OTHER PUBLICATIONS

De Lara Pedroso Daniela, Thomazini Marcelo, Barrozo Heinemann Riana Jordão, Favaro-Trindade Carmen Sílvia, "Protection of Bifidobacterium lactis and Lactobacillus acidophilus by microencapsulation using spray-chilling", International Dairy Journal, 2012, pp. 127-132, vol. 26 No. (2), Brazil.

De Lara Pedroso Daniela, Dogenski M. Thomazini Marcelo, Barrozo Heinemann Riana Jordão, Favaro-Trindade Carmen Sílvia, "Microencapsulation of *Bifidobacterium animalis* subsp. *lactis* and Lactobacillus acidophilus in cocoa butter using spray chilling technology", Brazilian Journal of Microbiology, 2013, pp. 777-783, vol. 44 No. (3), Brazil.

MacLean, N., Khadra, I., Mann, J., Abbott, A., Mead, H., & Markl, D. (2022). Formulation-dependent stability mechanisms affecting dissolution performance of directly compressed griseofulvin tablets. International Journal of Pharmaceutics, 631, 1-10. https://doi.org/10.1016/j.ijpharm.2022.122473.

Dickinson, E. (2007). Food colloids . . . how do interactions of ingredients control structure, stability and rheology? Current Opinion in Colloid & Interface Science, 12(4-5), 155-157. https://doi.org/10.1016/j.cocis.2007.08.003.

Bollom, M. A., Clark, S., & Acevedo, N. C. (2020). Edible lecithin, stearic acid, and whey protein bigels enhance survival of probiotics during in vitro digestion. Food Bioscience, 39, 1-7. https://doi.org/10.1016/j.fbio.2020.100813.

* cited by examiner

PROBIOTIC MICROCAPSULE

FIELD OF THE INVENTION

The technological development is related to the preparation of capsules, mainly the encapsulation of probiotic-type microorganisms to be used in functional foods.

RELATED BACKGROUND ART

Although the use of edible coatings and films to preserve food quality is not a new concept, research in academia, government and private industry laboratories have recently intensified its development due to the growing demand for high quality foods. In the same sense, the use of probiotic bacteria in foods is of growing interest, given it has the purpose of providing beneficial effects on health, where traditionally, lactic acid bacteria have been used in refrigerated dairy matrices which maintain the viability of these microorganisms until the end of the product's shelf life.

Among the available technologies to protect microorganisms in different applications, there is microencapsulation, a technology used to maintain the viability of probiotic bacteria during processing and storage of food products. Currently there are commercial developments of traditional probiotics. However, different operations such as heat treatment, homogenization, pH, acidity, oxidation, etc. to which foods are subject, as well as shelf life, may affect the survival of probiotics in the final product and their performance at a functional level (Maathuis, Keller and Farmer, 2010; Corona-Hernández et al., 2013).

For example, US2007/0098847 describes granules that are stable for 3 months at room temperature from *Lactobacillus casei* and a 50/50 mix of stearic acid and palmitic acid. As disclosed in the patent application, these granules may be incorporated into standard milk, fermented milk, fermented milk products, fruit and vegetable juices.

Also U.S. Pat. No. 8,871,266 relates to encapsulated probiotic bacteria formulations, wherein the encapsulating matrix is formed by a mixture between protein and carbohydrate and where the bacteria is added as a liquid concentrate or in lyophilized form to the encapsulating matrix. In said method, the probiotic is dispersed in an oil and then in a mix of protein and carbohydrate film formers. Encapsulation of the probiotic is accomplished by dispersing the microorganism in oil, which is subsequently dispersed into a film-forming protein and a carbohydrate (Strategy 3). In Strategy 3, once the microorganism is added to the oil and dispersed in the protein-carbohydrate mix, it is spray dried at a temperature between 120 and 160° C.

However, there are currently few alternatives for the encapsulation of sporulated probiotics for application in both solid and liquid matrices with high water activity. The technological development of the invention proposes a microcapsule, in which a spore probiotic is stabilized by means of at least one coating, which inhibits or retards the germination of the spore at room temperature, in such a way that it does not negatively alter the matrix in which it is incorporated.

BRIEF DESCRIPTION OF THE INVENTION

The present application is directed to a microcapsule of a probiotic encapsulated in a lipid sphere and coated with a protein film, thus preventing the microorganism from migrating outside and avoiding the generation of undesirable changes to the matrix where it is incorporated.

DETAILED DESCRIPTION OF THE INVENTION

Probiotic Microcapsule

Figure 1:
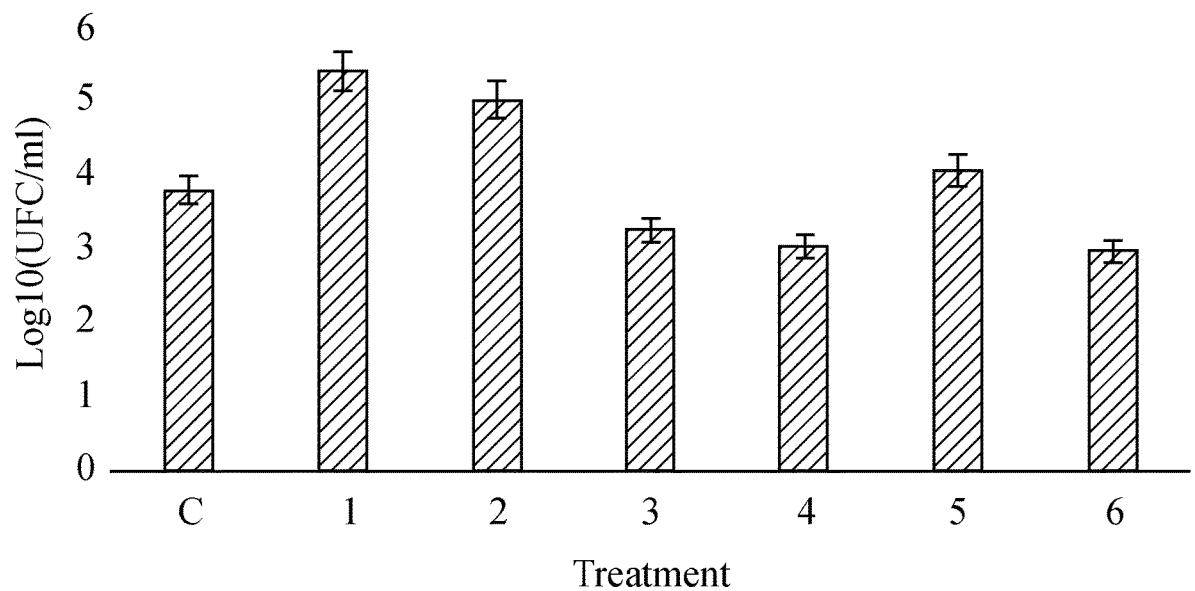
FIG. 1 Spore count released into the liquid medium for each of the treatments shown in Table 3.

The present application is directed to a microcapsule of a probiotic encapsulated in a lipid sphere and coated with a protein film that prevents the migration of the microorganism outside thus not generating undesirable changes to the matrix where it is incorporated, and a further process for the production thereof.

Thus, in the context of the present invention, a probiotic microcapsule is understood as one comprising a lipid sphere coated by a protein film; wherein the lipid sphere comprises a sporulated probiotic and a lipid wall material; and wherein the protein film comprises a protein material, a carbohydrate and water.

Lipid Sphere

The microcapsule lipid core, lipid sphere or sphere is composed of at least two elements: an active ingredient and a wall material. The active ingredient may be a microorganism, an ingredient of interest such as an aroma, a flavor, a coloring, a bioactive ingredient (antioxidant, energizer, tranquilizer, adaptogen, memory enhancer, mood modulator, among others) or combinations thereof. For the purposes of the present invention, "sphere" means the solid phase of the product, where the active ingredient is found.

The active ingredient is a microorganism, preferably a probiotic microorganism as defined by NTC 805 of 2006, International Dairy Federation 1997 or the World Health Organization. A probiotic refers to a living microorganism that, when supplied in the diet and ingested in sufficient quantity from a human or other animal, exerts a beneficial effect on health, beyond nutritional effects.

Preferably, the probiotic microorganism is a sporulated or spore-forming probiotic. When the probiotic microorganism is spore-forming, it has advantages over those without this capacity, because as an active ingredient, it does not require cold chain or dehydration processes and has greater versatility in the development of functional foods outside the refrigerator. The term "spore" refers to the resistance structure to extreme conditions (temperature above 60° C. and nutrient limitation), which after germination under favorable conditions, gives rise to a plant cell.

For purposes of the present invention, the sporulated probiotic is selected from the genus Bacillus, Paenibacillus, Brevibacillus or related genera. In one embodiment, sporulated probiotics are selected from strains of B. subtilis, B. indicus, B. licheniformis, B. clausii, B. pumilus, B. polyfermenticus, B. cereus, B. coagulans, Brevibacillus laterosporus, Paenibacillus polymyxa, and combinations thereof. The inventors noted that the spore is a microorganism in a dormant state, and once environmental conditions promoting growth are present, the spores will germinate and grow and multiply at different times.

The probiotic microorganism in the capsule has a sufficient bacterial concentration to exert a beneficial effect on health. In general, the concentration may be around 15 trillion spores per gram, which is understood to be around +/−5% of the concentration value. In particular, the sporulated probiotic has a concentration between $1.5 \times 10^6$ and $1.5 \times 10^8$ CFU/g in the microcapsule.

The sporulated probiotic is between 0.1 and 8% in the lipid sphere, between 0.1 and 5%, and between 0.1 and 3%. It must be considered that the more concentrated the capsule is, the higher the concentration gradient with respect to the medium, and the more the microorganism will want to migrate. Unless otherwise implied from the context or the normal in the art, all parts and percentages of this Specification are based on weight.

The microorganism is mixed with a wall material to form a lipid sphere, so it does not dissolve in water. The wall material is a lipid with a melting point below 40° C., so it dissolves in contact with stomach lipases and the microorganism may be released.

The lipid of the wall material is for example wax, oil or fats or a combination thereof. If the wall material is an oil it may be selected from, but is not limited to, sunflower oil, soybean oil, corn oil, cottonseed oil, coconut oil, palm kernel oil, palm oil, African palm oil, palm seed oil, safflower oil, canola oil, peanut oil, sesame oil, linseed oil (flax), and mixtures thereof. Possible waxes include, but are not limited to, beeswax, carnauba wax, candelilla wax, cocoa butter, peanut butter, and mixtures thereof.

Among other possible wall materials that are in the lipid sphere are lecithin, palm stearin, palmitic acid, stearic acid, shellac, gelatin, agar, gellan gum, pectin, alginate and mixtures thereof, among others.

The lipid wall material is found in the lipid sphere ranging between 92 and 99.9%, between 97 and 99.9%, or between 98 and 99.9%.

Protein Film

The protein film, coating matrix, protein coating or protein matrix has, among others, the characteristic to protect the lipid sphere and to reduce, delay or prevent the release of sporulated microorganisms. During the microcapsule production process, a film, coating or matrix is formed that embeds the lipid sphere or forms a film around it. The microcapsule comprises at least one protein film. The protein film is hydrophobic and impermeable or semi-hydrophobic and partially impermeable.

For the purposes of this invention, "protein film" is understood to be any type of material used as a coating, wrapping or separation layer for different foods, in such a way as to extend the product's shelf life and that may can be consumed without risk to human or other animal health. Each film or coating material provides a structure, mechanical resistance, solubility and other characteristic properties. An edible film or coating provides sterility to the food surface and prevents the loss of important compounds, in this case, the microorganism. In general, its thickness must be thin enough so that its particle size does not increase and is not perceptible in the mouth but thick enough so that it does not allow the migration of microorganisms.

The protein film comprises at least one protein material and at least one carbohydrate. This protein material is selected from, milk protein, whey, egg white, sodium caseinate, gelatin and combinations thereof, wherein the egg white is egg albumin, and whey is whey protein, and wherein the protein film further comprises lecithin and polysorbates. Protein material may or may not be lyophilized. The protein material is in the protein film between 1 and 40%, between 1 and 30%, or between 5 and 25%.

The carbohydrate may be of any kind commonly used in the food industry or in the pharmaceutical industry, preferably of high molecular weight, i.e. greater than 70000 Da. The carbohydrate is selected from, but not limited to lactose, maltodextrin, polyethylene glycol, starch and modified starch. When the carbohydrate is starch, it is selected among modified starch, pregelatinized starch, ungelatinized starch, native corn starch, modified corn starch, native yucca starch, modified yucca starch, and combinations thereof. The carbohydrate is in the protein film between 1 and 60%, between 10 and 50%, or between 20 and 35%.

Additionally, the protein film also includes water, wherein the water is in the protein film by more than 30%, between 40 and 75%, between 45 and 60%, between 45 and 75% or between 55 and 75%. Water acts as a carrier between the carbohydrate and the protein material, allowing crosslinking in the protein film.

Probiotic Microcapsule Production Process

The method of obtaining the invention microcapsules is carried out in two large parts: the formation of a lipid sphere and the coating of said sphere with a protein film. Wherein first, a sporulated probiotic is mixed with a wall material and a sphere is obtained, and second, a protein material, a carbohydrate and water are mixed forming a protein film. Finally, the sphere is coated with the homogenized protein film.

First, the lipidic spheres (core) are made from at least one microorganism and at least one wall material by mixing them. For the formation of such a sphere it is necessary that the wall material is in a liquid or molten state, so the microorganisms are incorporated into the medium, generating a multilayer. The conditions for the lipid wall material to be in a liquid or molten state depend on the melting point of its component or mixture of components. For example, before mixing, the wall material is brought to a melting point between 23 and 130° C., 35 and 80° C., or 45 and 65° C.

The mix between the microorganism and the wall material may be obtained for example by mechanical or magnetic stirring, using among others, radial stirrers, axial stirrers, propeller stirrers, paddle stirrers, vertical stirrers, horizontal stirrers, inclined stirrers, off-center stirrers or other stirrers known to a normally skilled person. If necessary, the mix may be obtained at temperatures ranging between 20 and 90° C., between 35 and 80° C. or, between 45 and 65° C.

Subsequently, the spheres are formed by manual methods such as pipettes, micropipettes or nanopipettes, automated methods by means of an encapsulator or spherifier, or any other method known to a normally skilled person in sphere formation. In one embodiment, the molten or liquid wall material is first put into a liquid state and then, the microorganism is added.

On the other hand, a protein material, starch and water are mixed until a protein film is obtained. Such a mix may be carried out, for example, by mechanical or magnetic agitation, using, among others, radial agitators, axial agitators, propeller agitators, paddle agitators, vertical agitators, horizontal agitators, inclined agitators, off-center agitators, or other agitators known to any normally skilled person.

It is expected that from the mixing process between the protein material, the carbohydrate and water, there will be a crosslinking process that on one hand, generates a protein film with stronger links between the compounds, and on the other hand, allows for a physical interaction with the surface of the lipid material (such as adhesion or absorption). Preferably, the components of the protein film are mixed in dispersion equipment such as an agitation plate or an Ultra-turrax®, with agitation conditions between 100 and 20000 RPM, between 300 and 10000 RPM, or between 500 and 9000 RPM, and a temperature ranging between 35 and 75° C., between 45 and 60° C., or between 48 and 58° C.

Later, the homogenization of the protein film is carried out, for example by means of micro fluidization, where crosslinking is favored and the particle size is reduced in such a way that the finer the crosslinking, the fewer pores that allow the release of the spores. The pressure of the microfluidizer should be greater than 9000 psi, greater than 9500 psi or greater than 10000 psi.

In addition, the protein film is subject to a denaturation of the proteins in the coating mixture, before being applied to the spheres, by means of heat treatments, chemical treatments or enzymatic treatments or a combination thereof. Denaturation is understood as the process in which the quaternary, tertiary and secondary structures of the protein are altered.

In another embodiment in which the denaturation is carried out by means of heat treatment, the chamber where the atomization is carried out is at a temperature that guarantees a certain degree of denaturation of the protein, for example ranging between 20° and 100° C., between 30° and 70° C., or between 40° and 60° C., and for a period between 2 and 80 minutes or between 20 and 40 minutes, so the protein film is fixed to the lipid sphere. Preferably, heat treatment is performed on the protein film at 30° C. for one hour. If the previous conditions are not fulfilled (higher temperatures and longer periods of time) it is possible that the lipid sphere will melt and the release of probiotic microorganisms may not be avoided at the right time or, on the contrary, a total coating of the lipid sphere may not be achieved.

Finally, coating is performed where individual particles or droplets of solid or semi-solid material (the core) are surrounded or coated with a continuous film of protein material (the coating) to produce capsules in the micrometer to millimeter range.

Coating may be performed by chemical, physicochemical or physical-mechanical techniques such as spray drying, cold drying, freeze drying, dipping, coacervation and extrusion, suspension, dispersion, emulsion and polymerization, layer-by-layer assembly, sol-gel encapsulation, supercritical CO2 extraction, spray drying, fluid bed coating or encapsulation, among others. In one embodiment, the coating is done by fluidizing the lipid sphere and spraying the protein film on the lipid sphere.

Throughout the fluidization of the lipid sphere and the spraying of the protein film, the sphere or core solidifies in such a way that the protein film remains fixed on its surface. In one embodiment, the fluidization of the lipid sphere and the spraying of the protein film is done by spray-chilling or atomization technology where the hot sphere (molten wall material incorporating the microorganism) is sprayed onto a stream of cold air solidifying the capsule. As the protein film cools, a layer forms around the sphere (core). The spraying is performed in a protein film to sphere ratio between 1:10 and 1:15.

In one embodiment of the process described above, this method includes (a) mixing a sporulated probiotic with a molten or liquid phase lipid wall material to obtain a lipid sphere; (b) mixing a protein material, a starch and water to form a protein film; (c) homogenizing the protein film; and (d) fluidizing the lipid sphere of stage (a) and spraying the protein film of stage (c) onto the lipid sphere.

The capsules obtained by the process described above are microcapsules of micrometric size (>1 μm), spherical shape and a particle size between 1 and 4000 μm, between 500 and 4000 μm, smaller than 400 μm (small), between 400 μm and 1200 μm (medium) or between 1180 μm and 2800 μm (large).

Uses

The probiotic microcapsules of the invention may be used to obtain products containing sporulated microorganisms, for example in the processing of food, medications, cosmetics and biological products for agricultural use and for bioremediation.

Particularly the invention refers to probiotic microcapsules to be used in food matrices to be ingested by humans or other animals, in such manner that the components thereof must be approved for human or animal consumption. Food matrices may be solid or liquid phase. Preferably the use of the microcapsule in a liquid or solid matrix that does not require refrigeration, especially with matrices whose pH is below 5.0.

For purposes of the present invention it is understood that the liquid matrix is the liquid phase, in which the microcapsule is incorporated. Preferably the liquid matrix in which the microcapsule of the invention is included has a pH between 4 and 7, between 4.5 and 6.5, or less than 5.

The liquid matrices may be dairy or non-dairy. For example, microcapsules may be added to functional foods and/or beverages, and/or dietary supplements including the microcapsules of the invention. Functional beverages include but are not limited to fruit-based beverages (BBF), vegetable-based beverages, water, milk, dairy-based beverages, flavored dairy-based beverages (BLS), water-based beverages, milk-based beverages, carbonated beverages or non-carbonated beverages.

Fruit or vegetable-based drinks may include one or more fruit or vegetable extracts. Wherein an extract is defined as a juice, nectar, puree, or pulp of the corresponding fruit or vegetable. The extract may be fresh, raw, processed (e.g., pasteurized), or reconstituted. The fruit extract is selected from but not limited to apple juice, pineapple juice, citrus juice (such as orange, tangerine, grapefruit, lemon, tangelo, etc.) cranberry juice, noni juice, acai juice, goji juice, cranberry juice, blackberry juice, raspberry juice, pomegranate juice, grape juice, apricot juice, peach juice, pear juice, mango juice, passion fruit juice, and guava juice. The vegetable extract is selected from but not limited to aloe vera juice, beet juice, carrot juice, celery juice, kale juice, spinach juice, tomato juice, ginger juice, and wheatgrass juice.

EXAMPLES

Example 1

Evaluation of Wall Materials

For the formation of the lipid sphere, the following were evaluated as components of wall materials: beeswax, palm oil, palm kernel, palm stearin and peanut butter, and their combinations shown in Table 1, with a high pH categorical factor of 6.5 and low pH of 4.5. The fats and waxes were heated with constant agitation until they were melted. Subsequently, 0.1 g of sporulated microorganism was added to 10 g of the wall material. Spheres were made with a micropipette and 15 spheres were placed in 5 mL of MRS for 0, 4, 6 and 12 days at 25° C.

In order to count microorganisms in the aqueous phase, 1 mL was taken from each tube and serial dilutions were made in MRS medium. For the solid phase, lipid spheres were vacuum filtered and placed in 9004 and 2% sodium citrate, heated and serial dilutions were made.

TABLE 4

Protein film mixes with the highest percentage reduction of viable spore cells in the lipid spheres at day 5 of incubation at 4° C.

| No. | A | B | C | D | Percentage reduction | Desirability |
|---|---|---|---|---|---|---|
| 1 | 0.1 | 0.061 | 0.276 | 0.564 | 119.048 | 1 |
| 2 | 0.1 | 0.061 | 0.299 | 0.54 | 116.112 | 1 |
| 3 | 0.1 | 0.09 | 0.302 | 0.508 | 123.619 | 1 |
| 4 | 0.097 | 0.069 | 0.293 | 0.541 | 118.729 | 1 |
| 5 | 0.097 | 0.11 | 0.29 | 0.504 | 128.737 | 1 |
| 9 | 0.058 | 0.058 | 0.322 | 0.562 | 97.600 | 1 |
| 10 | 0.090 | 0.106 | 0.304 | 0.500 | 107.673 | 1 |
| 11 | 0.050 | 0.050 | 0.350 | 0.550 | 134.651 | 1 |
| 12 | 0.099 | 0.132 | 0.267 | 0.502 | 118.455 | 1 |
| 13 | 0.100 | 0.115 | 0.269 | 0.516 | 122.907 | 1 |
| 14 | 0.060 | 0.054 | 0.324 | 0.562 | 97.956 | 1 |
| 15 | 0.050 | 0.083 | 0.350 | 0.517 | 108.737 | 1 |
| 16 | 0.061 | 0.059 | 0.350 | 0.529 | 104.282 | 1 |
| 17 | 0.085 | 0.086 | 0.284 | 0.545 | 98.297 | 1 |
| 18 | 0.050 | 0.050 | 0.330 | 0.570 | 112.022 | 1 |
| 19 | 0.087 | 0.087 | 0.306 | 0.519 | 103.278 | 1 |

TABLE 4-continued

Protein film mixes with the highest percentage reduction of viable spore cells in the lipid spheres at day 5 of incubation at 4° C.

| No. | A | B | C | D | Percentage reduction | Desirability |
|---|---|---|---|---|---|---|
| 20 | 0.050 | 0.050 | 0.325 | 0.575 | 107.071 | 1 |
| 21 | 0.086 | 0.112 | 0.290 | 0.512 | 104.615 | 1 |
| 22 | 0.060 | 0.061 | 0.327 | 0.551 | 97.940 | 1 |
| 23 | 0.089 | 0.104 | 0.279 | 0.527 | 105.386 | 1 |

A: Lyophilized egg white;
B: Sodium caseinate;
C: Modified corn starch;
D: Distilled water From the table above, lipid sphere numbers 1, 3, 5 and 6 were selected to assess the viable cells in Log (CFU/g) and consistency (qualitative).

| Quality category of the encapsulation material | |
|---|---|
| 1 | Low rigidity and difficult capsule handling. |
| 2 | Medium hardness and regular capsule handling. |
| 3 | Medium hardness and rigidity, good capsule handling. |
| 4 | High hardness and rigidity, good capsule handling. |

TABLE 2

Selected spheres to continue with the study

| No. | Viable cells Log (UFC/g) | Hardness | Desirability |
|---|---|---|---|
| 1 | 7.79 | 3.55 | 0.992 |
| 3 | 7.73 | 3.79 | 0.065 |
| 5 | 7.70 | 3 | 0.951 |
| 6 | 7.32 | 3 | 0.787 |

Example 2

Evaluation of Different Types of Starch

For the formation of the protein film, and in search of the optimal mixture of materials for the coating that would comply with the purpose of preventing the migration of spores from the lipid sphere to the aqueous matrix, in this case, a commercial product (on the one hand a flavored milk drink, from now on BLS, and on the other a fruit-based drink, from now on BBF), different types and concentrations of starch (carbohydrates), egg white and sodium caseinate (protein materials) were evaluated. Similarly, different homogenization techniques and heat treatments were used, as described in Table 3.

TABLE 3

Coating production with different concentrations, homogenization and denaturation techniques of the protein film components.

| | Starch | Egg albumin | Sodium caseinate | Mixing and homogenization | Coating method | Drying | Heat treatment |
|---|---|---|---|---|---|---|---|
| C | NA | NA | NA | NA | NA | NA | NA |
| 1 | Native Yucca: 25% | 5% | 5% | Shaking plate 500 RPM, 50° C. | Immersion | NA | 70° C.-3 min |
| 2 | Modified corn: 25% | 5% | 5% | Shaking plate 500 RPM, 50° C. | Immersion | NA | 70° C.-3 min |
| 3 | Modified corn: 25% | 5% | 5% | Ultraturrax® 9000 RPM-microfluid | Immersion | Room temperature | 30° C.-1 h |
| 4 | Modified corn: 30%. | 10% | 10% | Ultraturrax® 9000 RPM-microfluid | Immersion | Room temperature | 30° C.-1 h |
| 5 | Native corn: 25% | 5% | 5% | Shaking plate 500 RPM, 50° C. | Immersion | Room temperature | 70° C.-2 min |
| 6 | Native Yucca: 25% | 5% | 5% | Shaking plate 500 RPM, 50° C. | Immersion | Room temperature | 70° C.-2 min |

Table 3 shows the different conditions that were evaluated in terms of concentration of protein film components, homogenization techniques and heat treatments.

Figure 2:
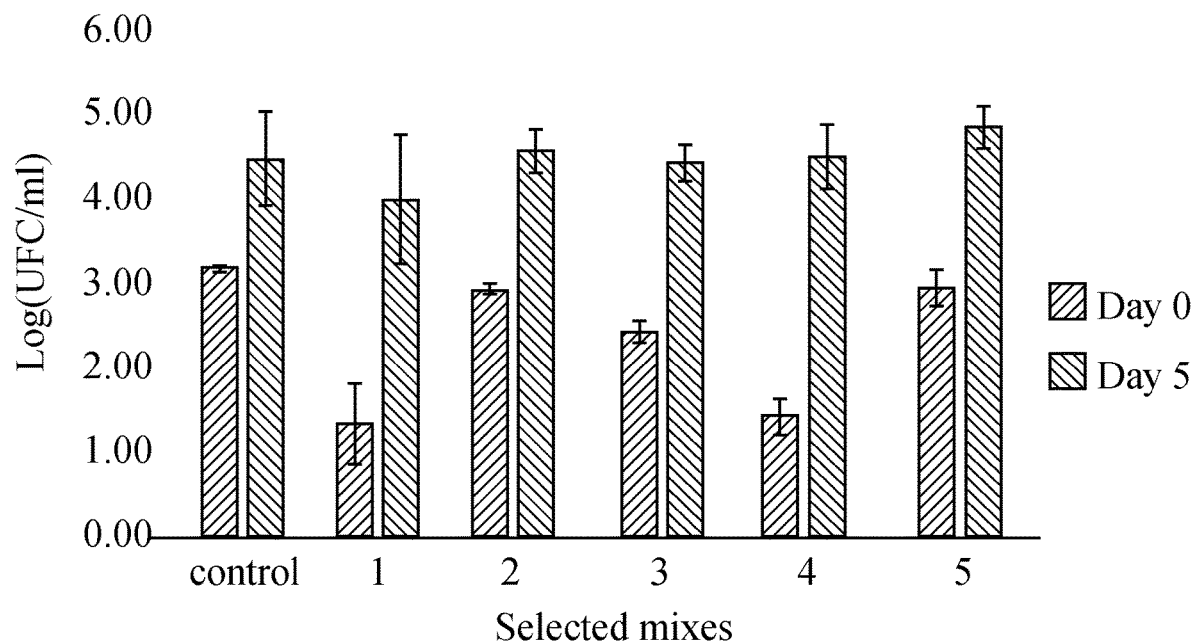
FIG. 2 Viable spore count in liquid medium; coating effectiveness test at 0 and 5 days.

Based on what is stated in FIG. 1, it may be observed how treatment 3 and 4 corresponding to the mix of egg white, sodium caseinate and modified corn starch, homogenized with Ultraturrax® and microfluidizer to which a low temperature (30° C.) heat treatment was applied for one hour was the most effective treatment to reduce the number of free spores in the commercial matrix obtaining lower counts than the control, possibly due to the fact that the homogenization processes present only in these treatments start the denaturalization of proteins and the gelification of starch, thus allowing a more effective adhesion between the lipid sphere and the protein film coating. Although temperature in the heat treatment was low, this allowed more water to be removed than a shorter heat treatment (2-3 minutes) at a higher temperature (70° C.).

Treatments 3, 4, 5 and 6 were different because they had an additional drying process at room temperature for 1 hour, which could allow the coating stabilization by decreasing its humidity. However, the heat treatment at high temperatures and short times present in tests 1 and 2 could affect the integrity of the sphere, melting it and allowing the migration of sporulated microorganisms to the environment, which explains why the counts are even higher than the control. Finally, facing the results, it is possible to establish that homogenization, drying time and corn starch are important factors when it comes to decrease the number of free spores from the lipidic spheres towards the food matrix.

Example 3

Evaluation of Coating Material Combinations

Mixes were made for protein materials, modified starch and water (A: lyophilized egg white; B: sodium caseinate; C: modified corn starch; D: distilled water). The individual effect and the interactions between the mixes of materials on the response variable: percentage reduction of CFU/ml of viable cells of the microorganism *Bacillus coagulans* Lactospore®, were analyzed at 5 days of incubation at 4° C. Viable cells correspond to the total number of viable cells present in the liquid phase (spores and germinable cells). During the set-up of the experiment, lipid spheres were made with a concentration of approximately $1.5\times10^8$ CFU/g of sporulated microorganism and inoculated in 15 mL of BLS.

Percentage reduction of free cells=((spore control (CFU)−spore treatment(CFU))/spore control (CFU))*100

TABLE 4

Protein film mixes with the highest percentage reduction of viable spore cells in the lipid spheres at day 5 of incubation at 4° C.

| No. | A | B | C | D | Reduction percentage | Desirability |
|---|---|---|---|---|---|---|
| 1 | 0.1 | 0.061 | 0.276 | 0.564 | 119.048 | 1 |
| 2 | 0.1 | 0.061 | 0.299 | 0.54 | 116.112 | 1 |
| 3 | 0.1 | 0.09 | 0.302 | 0.508 | 123.619 | 1 |
| 4 | 0.097 | 0.069 | 0.293 | 0.541 | 118.729 | 1 |
| 5 | 0.097 | 0.11 | 0.29 | 0.504 | 128.737 | 1 |
| 9 | 0.058 | 0.058 | 0.322 | 0.562 | 97.600 | 1 |
| 10 | 0.090 | 0.106 | 0.304 | 0.500 | 107.673 | 1 |
| 11 | 0.050 | 0.050 | 0.350 | 0.550 | 134.651 | 1 |
| 12 | 0.099 | 0.132 | 0.267 | 0.502 | 118.455 | 1 |
| 13 | 0.100 | 0.115 | 0.269 | 0.516 | 122.907 | 1 |
| 14 | 0.060 | 0.054 | 0.324 | 0.562 | 97.956 | 1 |
| 15 | 0.050 | 0.083 | 0.350 | 0.517 | 108.737 | 1 |
| 16 | 0.061 | 0.059 | 0.350 | 0.529 | 104.282 | 1 |
| 17 | 0.085 | 0.086 | 0.284 | 0.545 | 98.297 | 1 |
| 18 | 0.050 | 0.050 | 0.330 | 0.570 | 112.022 | 1 |
| 19 | 0.087 | 0.087 | 0.306 | 0.519 | 103.278 | 1 |
| 20 | 0.050 | 0.050 | 0.325 | 0.575 | 107.071 | 1 |
| 21 | 0.086 | 0.112 | 0.290 | 0.512 | 104.615 | 1 |
| 22 | 0.060 | 0.061 | 0.327 | 0.551 | 97.940 | 1 |
| 23 | 0.089 | 0.104 | 0.279 | 0.527 | 105.386 | 1 |

A: Lyophilized egg white;
B: Sodium caseinate;
C: Modified corn starch;
D: Distilled water The first five combinations (Numbers 1 to 5) of wall materials of the experimental design were taken since they contain a higher concentration of egg white, which is the material that most influences in the reduction of free microorganisms, which presented a higher percentage of reduction of UFC/ml according to the optimization of the model and the microcapsules with the spores of *Bacillus coagulans* Lactospore® at a concentration of approximately $1.5\times10^9$ UFC/g were elaborated. Finally, these microcapsules were inoculated in a milk matrix, 15 mL of BLS. Counts of the microorganisms of the solid and liquid phase were made at days 0 and 5.

As evidenced in FIG. 2, at day zero a reduction in the concentration of sporulated microorganisms is achieved in comparison with the control (uncoated spheres) for mixes 1 and 4 of almost two logarithmic units, while mixes 2 and 3 show almost no difference with the control, this is because although the concentration of materials in the mixture is very similar, the form of coating application is fundamental for the effectiveness and permanence of the layer and when this was applied manually did not present exactly the same conditions in all tests.

The difference that was evident for day zero disappears almost completely on day 5 for all the mixes, this is because the coating was found to be detached and separated from the lipid spheres in all the tests at the time of the counts, this may be due to the lack of affinity between the materials of the lipid sphere and the protein film, since the denaturalization process of the proteins was not reached, because the sphere fusion point was exceeded and deformed it; therefore, the expected crosslinking was not generated between the materials.

Figure 3:
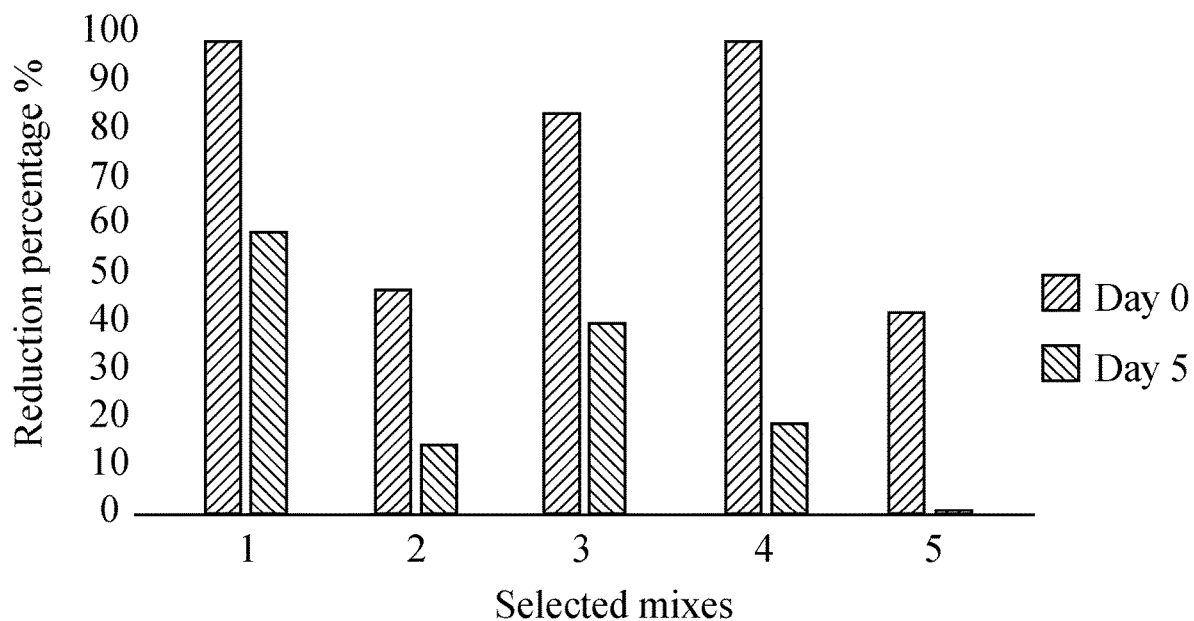
FIG. 3 Viable spore reduction percentage in liquid medium; coating compared to uncoated lipid spheres.

FIG. 3 shows the reduction percentage of the microorganisms in relation to the control. It may be seen that on day zero, the best mix for the coating is mixes 1 and 4, reaching almost 100% reduction, and in the same way on day 5, mixes 1 and 4 are the ones showing the greatest reduction, but mix 1 was the one showing more reduction compared to the control, and it is for this reason that it was the selected mix for the other tests.

Example 4 pH-Modified Coating

Figure 4:
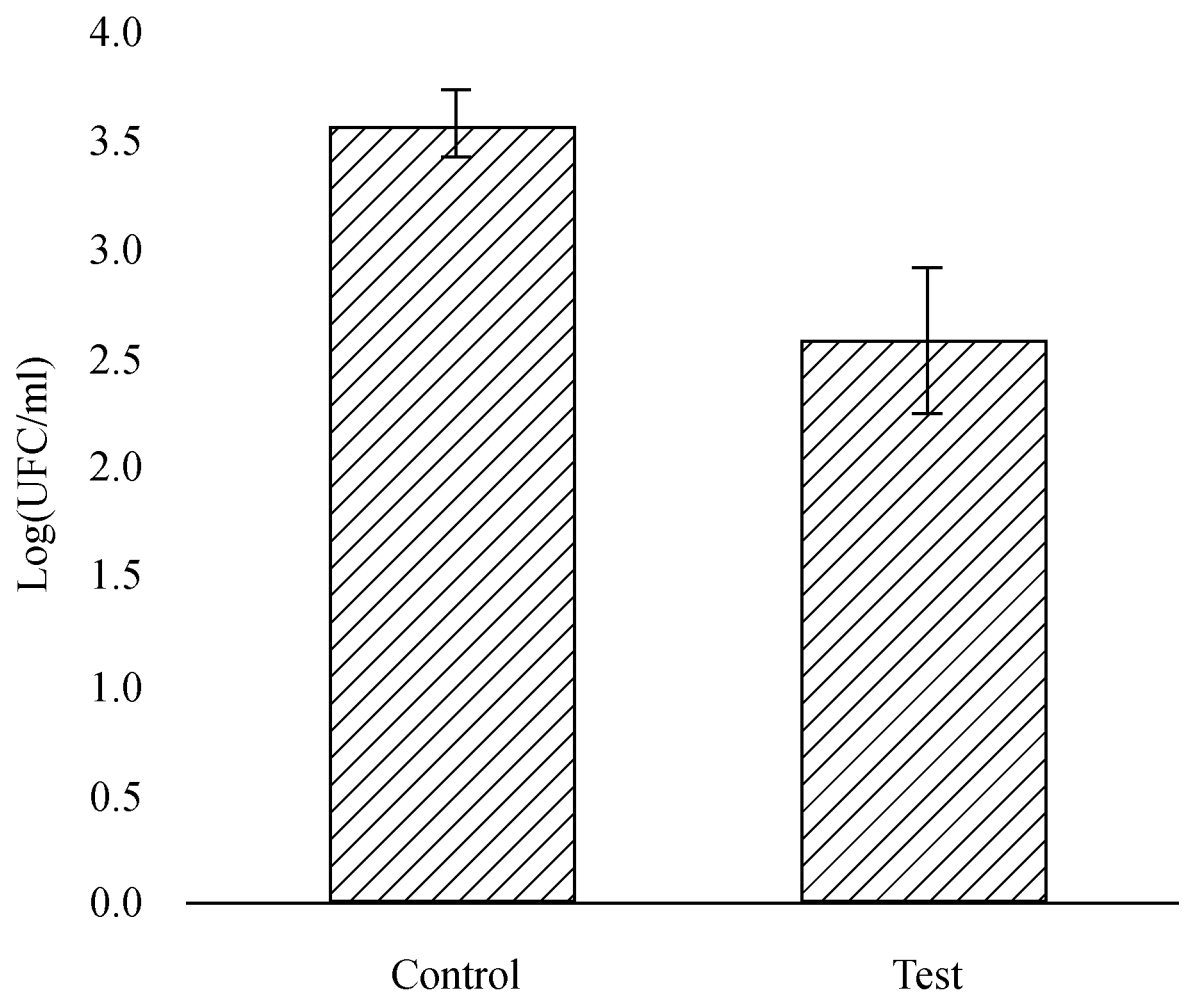
FIG. 4 Coating with a pH modification to 4.6 of the protein film to improve protein denaturation.

Taking into account for the coating mixture to be effective as a hydrophobic barrier and impermeable to the sphere of *Bacillus coagulans* Lactospore®, it is necessary to denature the proteins of the protein film and to gel the starch. In order to achieve denaturation, it is necessary to subject the proteins to high temperatures, however, these temperatures affect the integrity of the lipid spheres. Therefore, it was decided to denature the proteins of the coating mixture before applying it on the spheres, modifying the pH up to 4.6 and performing a heat treatment at 92° C. for 10 min. As it is shown in FIG. 4, this treatment improved the results by decreasing approximately one logarithmic unit the concentration of free spores compared to the control (FIG. 4).

Example 5

Lecithin Coating

In order to reduce the diffusion of the microcapsule in the aqueous medium (BLS), a test was carried out to elaborate the lipid spheres with beeswax with a mixture of 1% lecithin so it could be observed if there was any change with respect to the wax alone. The spheres were produced by extrusion with a weight of 0.6 g each and put in 15 ml of BBL, for each tube 6 spheres were added with an initial concentration of $1.5 \times 10^7$ UFC/g.

A parallel test was also carried out in which it was desired to study the effect of the size of the microcapsules in the diffusion, so the mixtures for BLS and BBF were taken and tests with small size (0.1 g) and medium size (0.3 g) were carried out. One gram of each size per tube was placed respectively in each one of the matrices (15 ml) and the microorganism concentration was measured.

Figure 5:
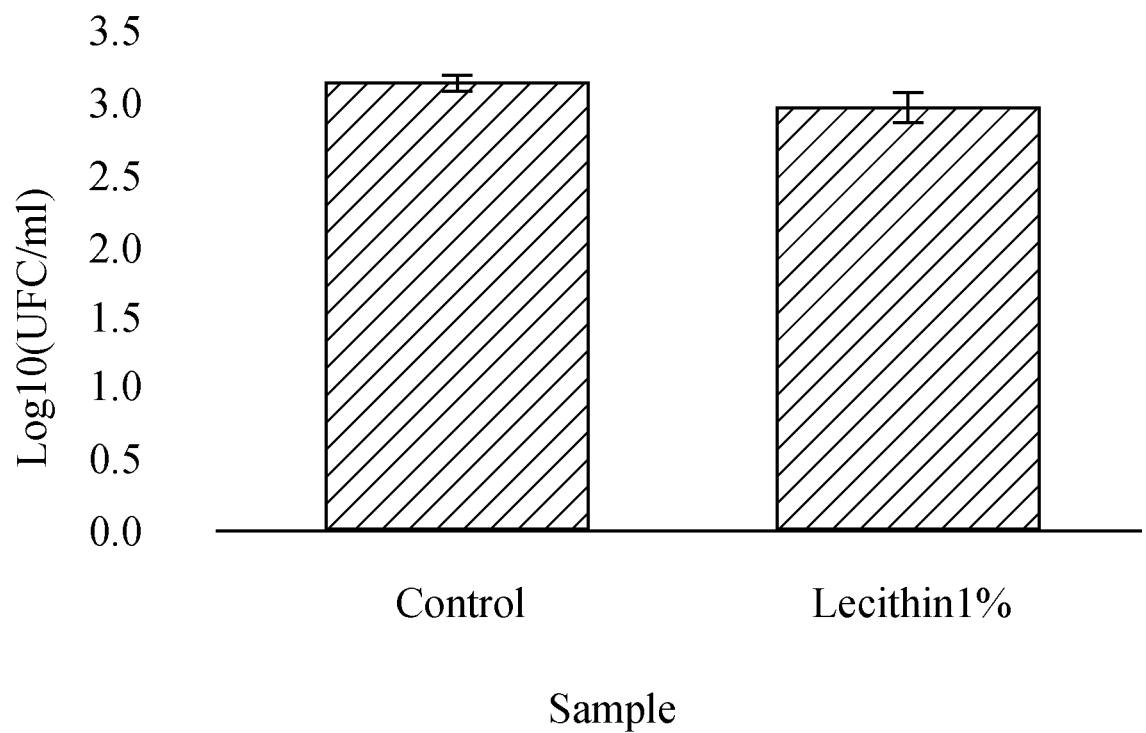
FIG. 5 Microorganism concentration in the liquid phase with lecithin coating.

As may be seen in FIG. 5, there is a small decrease in the concentration of microorganisms when lecithin is added to the wax, however, such a marked change is not evident. It is possible that by varying the concentrations of lecithin in the lipid mix there is a noticeable decrease in the concentration of microorganism diffused in the aqueous medium.

Figure 6:
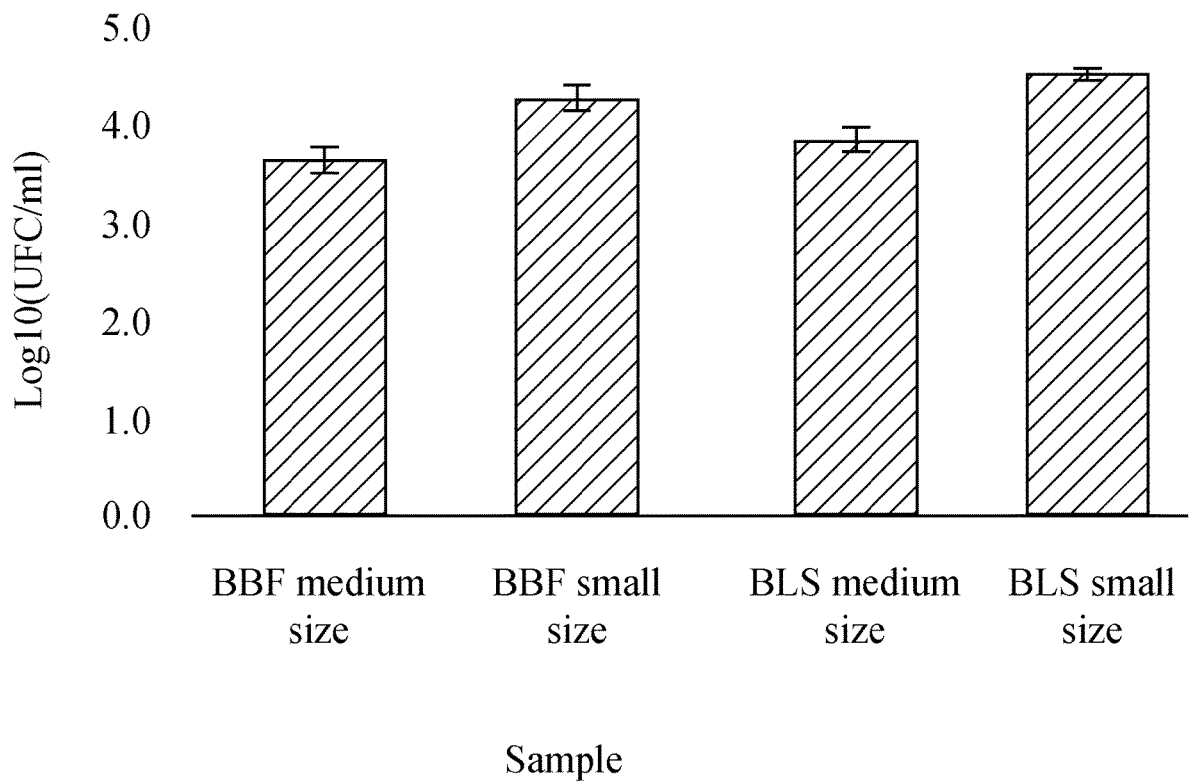
FIG. 6 Microorganism concentration in the liquid phase for different sphere sizes.

As observed in FIG. 6, the populations of microorganisms present in the solid phase for the small sizes in both the BBF matrix and the BLS were larger than in the medium size. This is due to the fact that the smaller the microcapsules, the larger the transfer area is compared to the medium size, allowing diffusion to occur quicker. Moreover, the path that microorganisms must make to leave the lipid sphere (from the center) is greater in the medium size than in the small one, which makes diffusion more difficult and delays migration.

Example 6

Sphere Size Diffusion Test

A diffusion test was carried out in which it was sought to observe the effect of microcapsules size on the microorganism diffusion in the liquid phase. Three sizes of microcapsules were selected and placed in the two matrices BBF and BLS: small size (microcapsule between 1180 µm and 2800 µm) medium (0.3 g microcapsule) and large (0.6 g/microcapsule) the microcapsules were made with beeswax, the large and medium sizes were made by extrusion while the small size was made in a Spray Cooling equipment built at the Universidad de la Sabana.

The microcapsules were placed in 15 ml of BLS and incubated for 5 days at refrigeration temperature (4° C.). The notation used for the test and the results may be found in FIG. 7. The microcapsules were prepared with an initial concentration of approximately $2.5 \times 10^7$ CFU/g.

Figure 7:
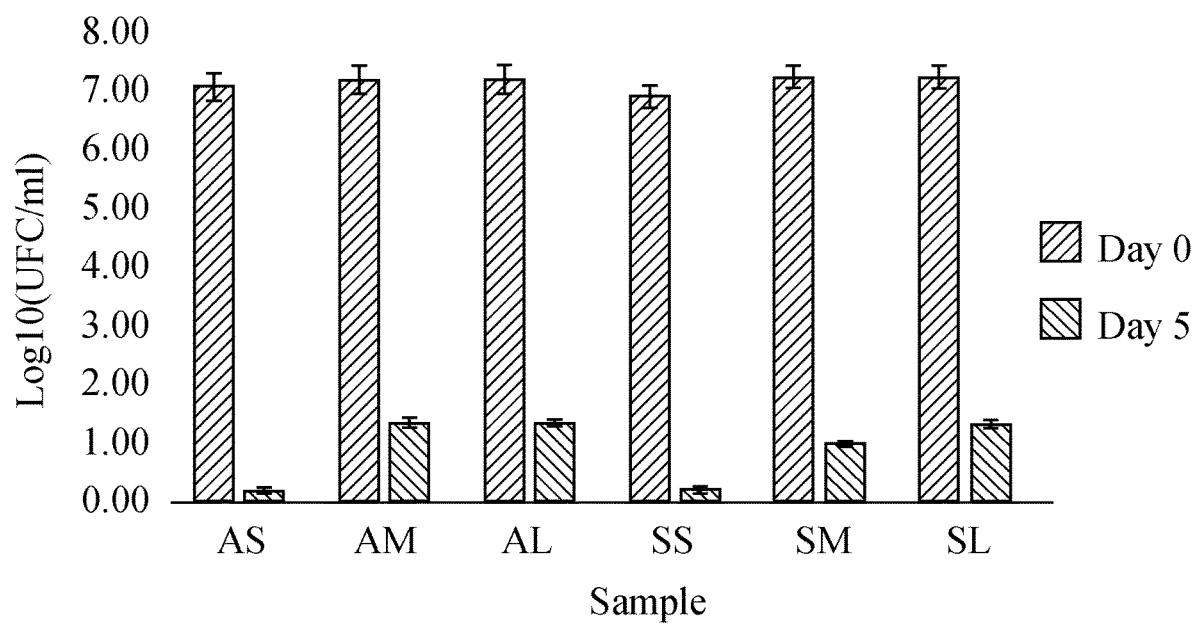
FIG. 7 Microorganism concentration in the solid phase; size test. AL (BLS large spheres), AM (BLS medium spheres), AS (BLS small spheres), SL (BBF large spheres), SM (BBF medium spheres) and SS (BBF small spheres).

As evidenced in FIG. 7 for time 0 there was no marked difference in the microorganism concentration within the microcapsules for any size, however, for day 5 the differences become more evident, for both BLS and BBF the concentration of microorganisms present in the small size microcapsules at the end of day 5 was lower than in the medium and large sizes, with a difference of up to almost 2 log units between the small and large size. This is due to the fact that the smaller the microcapsules, the larger the transfer area is compared to the medium and large size allowing the diffusion to occur faster. Moreover, the path that microorganisms must make to leave the lipid sphere (from the center) is greater in the medium and large size than in the small one, which makes the diffusion more difficult and delays the migration.

Example 7

Short Shelf Life (Fluid Bed)

Beeswax was chosen for a fluid bed coating test as it is easier to handle, due in part to its high melting point (65° C.), its greater availability and ease of commercial production; this beeswax was purchased from Quimicos Campota®. The wax was melted at 70° C., mixed with the microorganism sporulated at 5% and sprayed in the Spray Cooling built at Universidad de la Sabana and then coated in the HDB 15 Fluid Bed equipment (Baüer, Colombia) under the following conditions 15 minutes of mixing at 25° C. (conditioning), 52 minutes of atomization of the protein film that was sprayed in a ratio of 330 g of coating per 3300 g of lipid spheres of beeswax with microorganism which means a ratio of 1:10, the protein film was the one selected in FIG. 3 as the one presenting the highest percentage of reduction in terms of diffusion. Finally, a heating was generated in the fluid bed chamber for 30 minutes at 47° C. to promote the denaturalization of the coating proteins.

From the final product, 3 particle sizes were separated by sieving: microcapsules smaller than 710 µm (small), microcapsules between 710 µm and 1180 µm (medium) and microcapsules between 1180 µm and 2800 µm (large) which were placed in the commercial matrix (BLS and BBF of mandarin) during one week at two temperatures (room temperature 25° and refrigeration 4° C.) in which 4 points were measured (days 0, 2, 5 and 7) to determine the diffusion of the microorganism from the microcapsules to the matrix and the change in pH and soluble solids of the matrix. During the test, the changes that both matrices have only due to the influence of the microorganism at room temperature were also evaluated. Therefore, samples were inoculated at a similar concentration to the one present in the microcapsules and the viability of the microorganism was evaluated at the same time intervals and matrix properties, such as pH and soluble solids.

Figure 8:
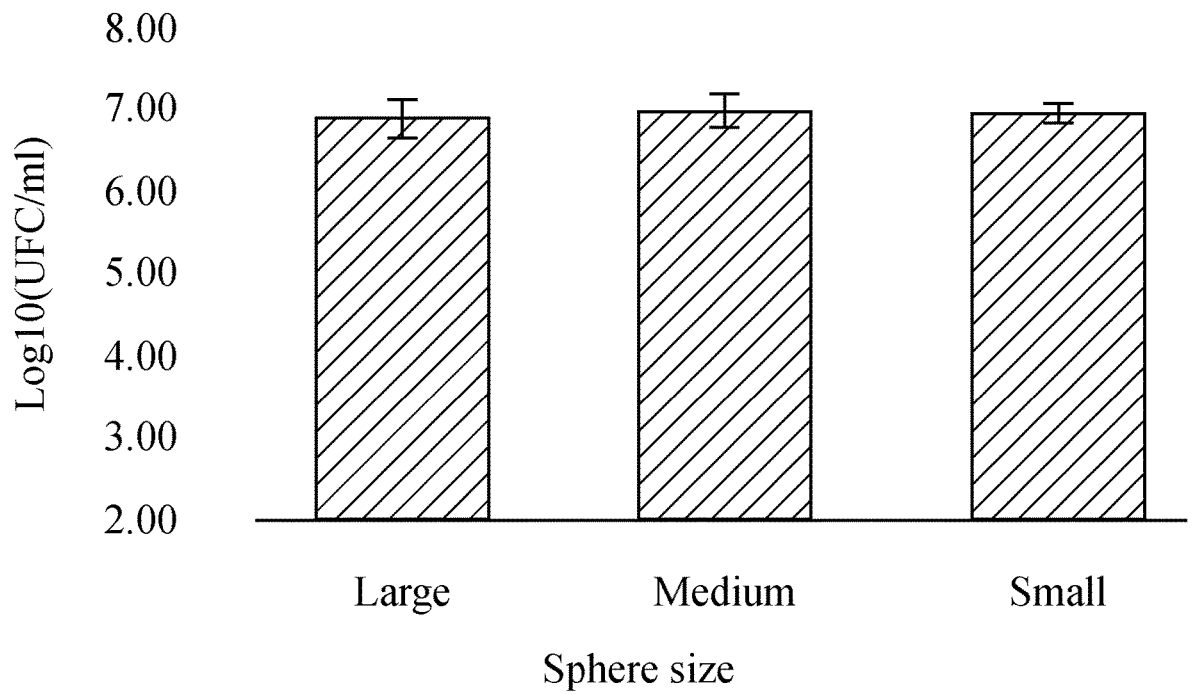
FIG. 8 Viable spore count within the different particle sizes obtained from the fluidized bed.

It is worth clarifying that the original concentration of microorganisms present in the different sizes of microcapsules does not vary independently of the size, as observed in FIG. 8.

Figure 9:
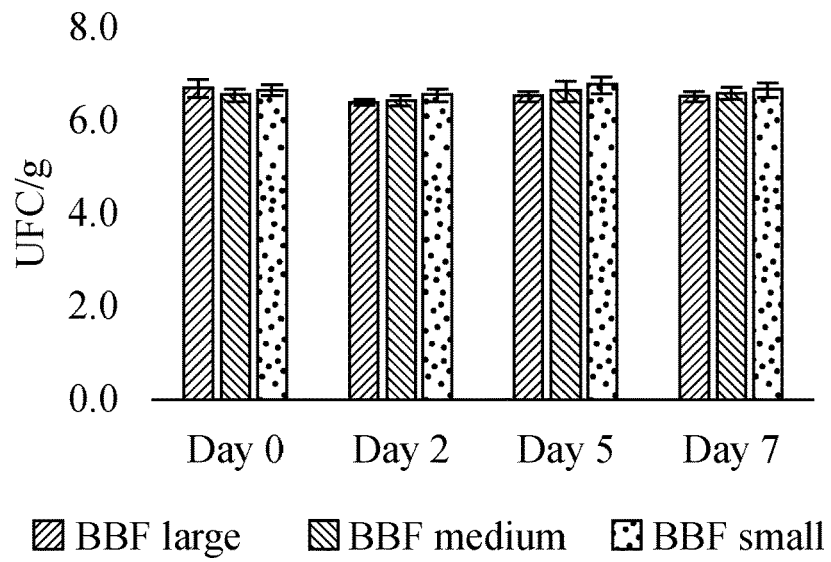
FIG. 9 Viable spore count in the solid phase present in the BBF matrix and viable spore count in the liquid phase present in the BBF matrix incubated at 4° C.
Figure 9:
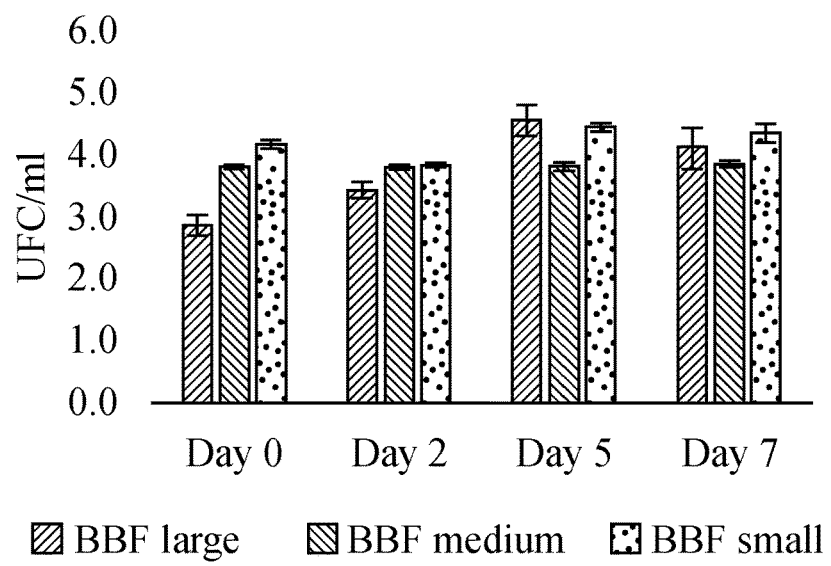

In FIG. 9, it may be noted that although the populations in the solid phase for the three sizes in the four monitoring points remained more or less constant at 6 log units, there was a progressive increase in the population in the liquid phase starting at approximately 2 log units and ending at 4 log units, this increase in the population in the liquid phase may be attributed to the reproduction of the population in the medium and one effect of this is the increase in the pH present in this matrix during the time of the test.

Figure 10:
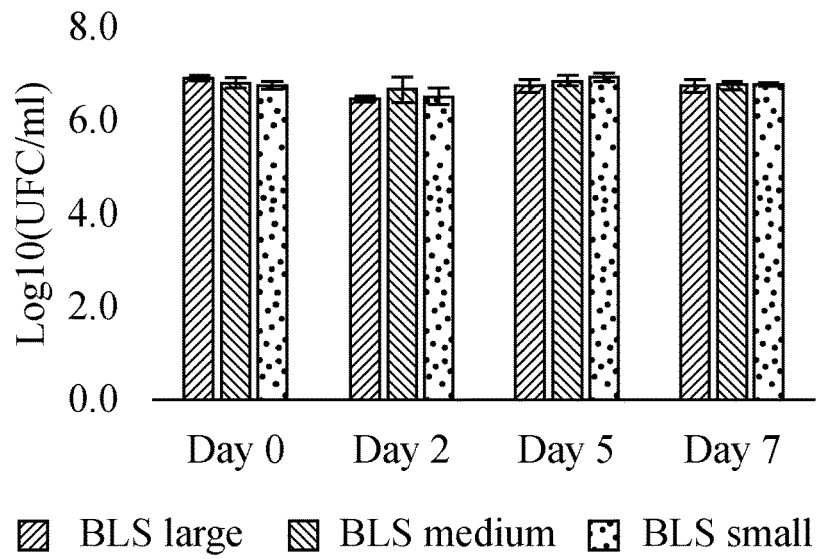
FIG. 10 Viable spore count in the solid phase present in the BLS matrix and viable spore count in the liquid phase present in the BLS matrix incubated at 4° C.
Figure 10:
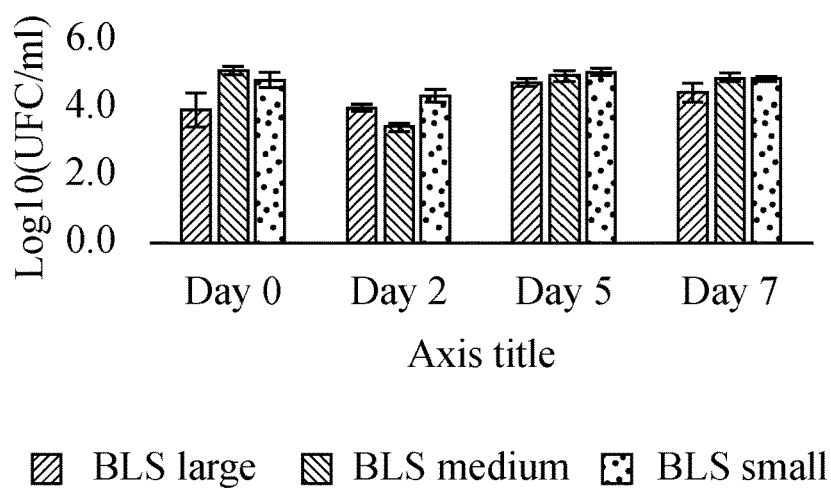

FIG. 10 similarly shows, as in the previous figures, that the population in the solid phase remained more or less constant at approximately 6 logarithmic units, but in the liquid phase, it remained more or less constant at 4 logarithmic units. In this case, there was also a greater diffusion of microorganisms in the microcapsules of medium and small size, even when the concentration of microorganisms was less in the medium sized than in the large sized (FIG. 8), given as explained previously, the contact area for diffusion is greater in the medium sized, and the distance that the microorganisms must travel from the center of the sphere is less than in the large sized.

Figure 11:
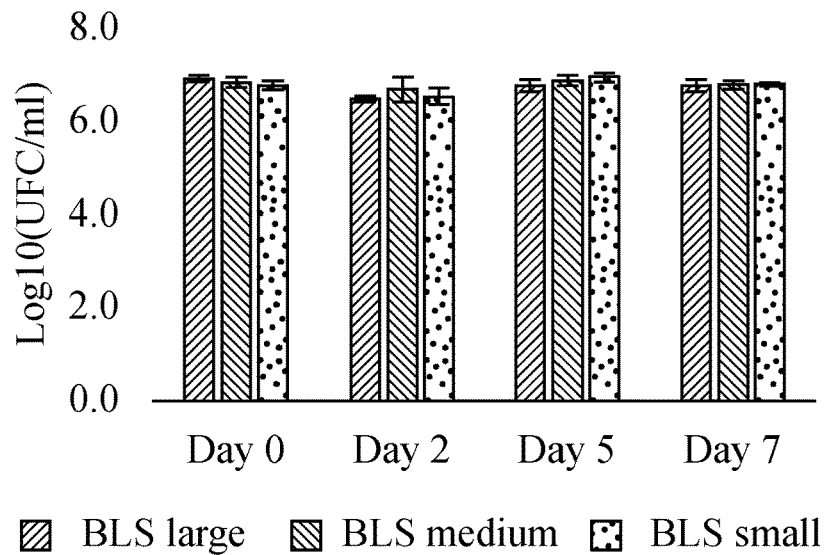
FIG. 11 Viable spore count in the solid phase present in the BBF matrix and viable spore count in the liquid phase present in the BBF matrix incubated at 25° C.
Figure 11:
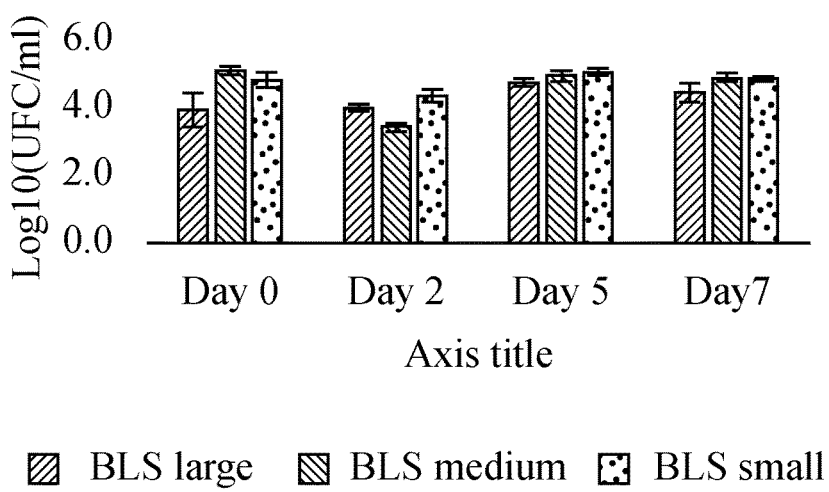

FIG. 11 shows the results of the different sizes of microcapsules for the BBF and BLS matrices at 25° C.; in the solid phase, the concentration of microorganisms is stable for 0 and 2 days, and a slight decay for the three sizes on days 5 and 7. Despite this, this change is not reflected in the concentration of microorganisms in the liquid phase, given this is maintained for the three sizes on the 7 days of the study.

Figure 12:
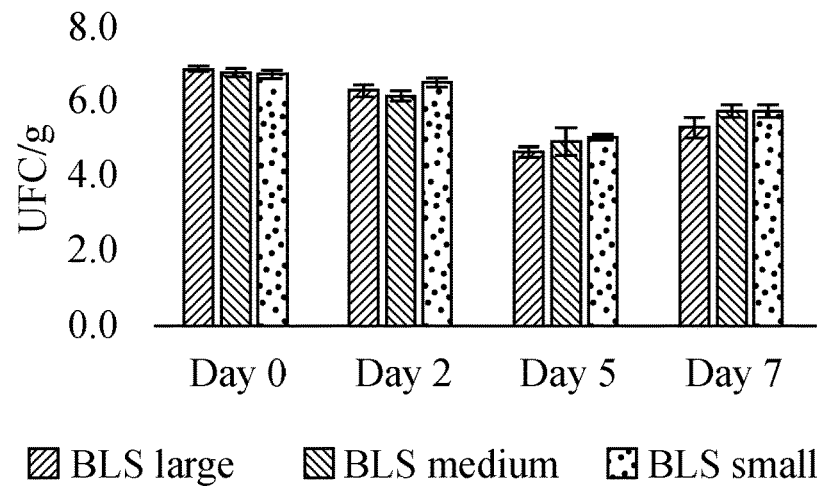
FIG. 12 Viable spore count in the solid phase present in the BLS matrix and viable spore count in the liquid phase present in the BLS matrix incubated at 25° C.
Figure 12:
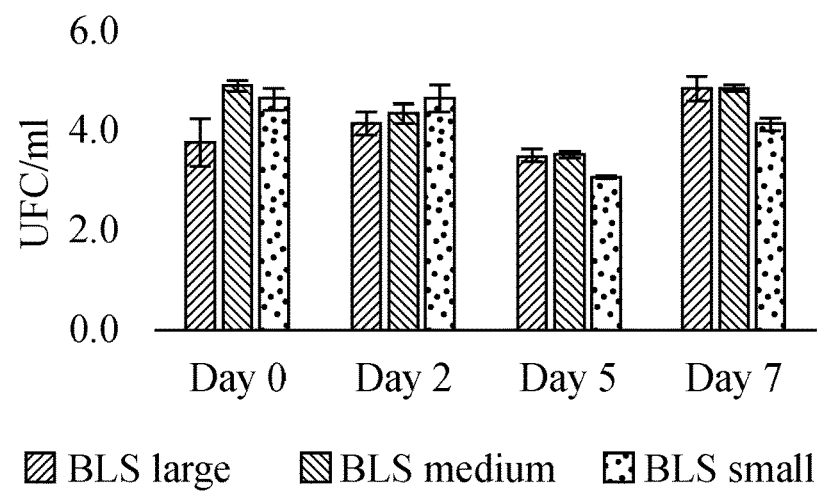

As in FIG. 11, FIG. 12 shows a small reduction in the population in BLS for days 5 and 7 in the solid phase while for the liquid phase in these same times there was also a slight decrease in the population, the sizes of the microcapsules maintained a more or less equal behavior among them, from the beginning in which there was an almost immediate diffusion of the microorganism to the environment.

Figure 13:
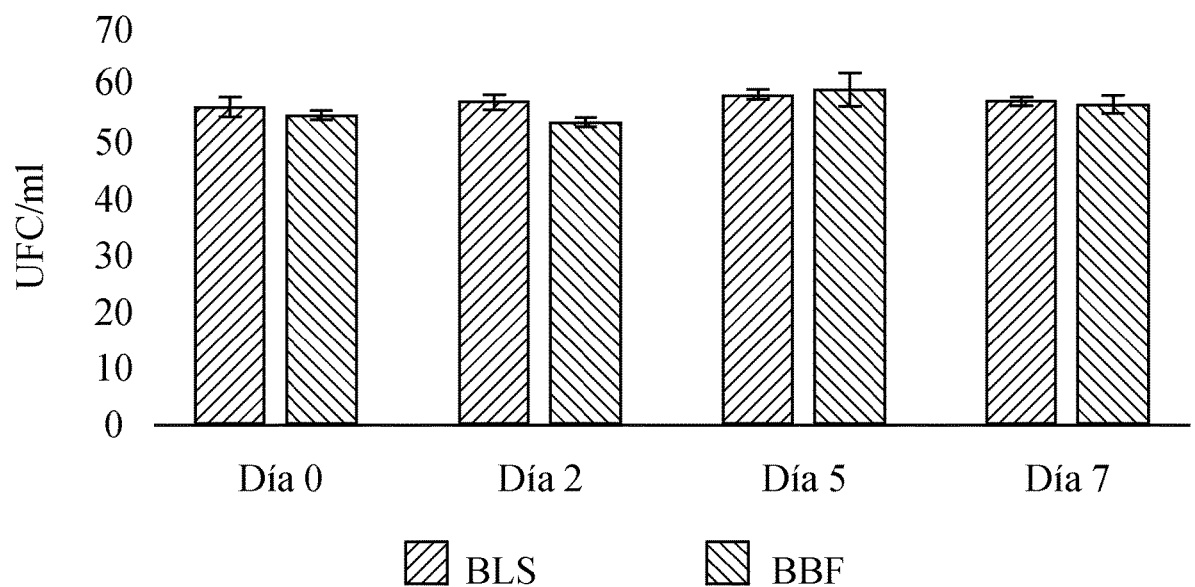
FIG. 13 Viable spore count in BBF and BLS matrices incubated at 25° C.

FIG. 13 shows the concentration of microorganisms present in both the BBF and BLS matrices that were deliberately inoculated to quantify the change in the environment due to this alone. The growth was similar in the BBF and BLS matrices, the BBF counts started at 5.5 and ended at 5.7 $Log^{10}(CFU/ml)$ while for the BLS the initial concentration was 5.7 and ended at 5.8 $Log^{10}(CFU/ml)$.

Figure 14:
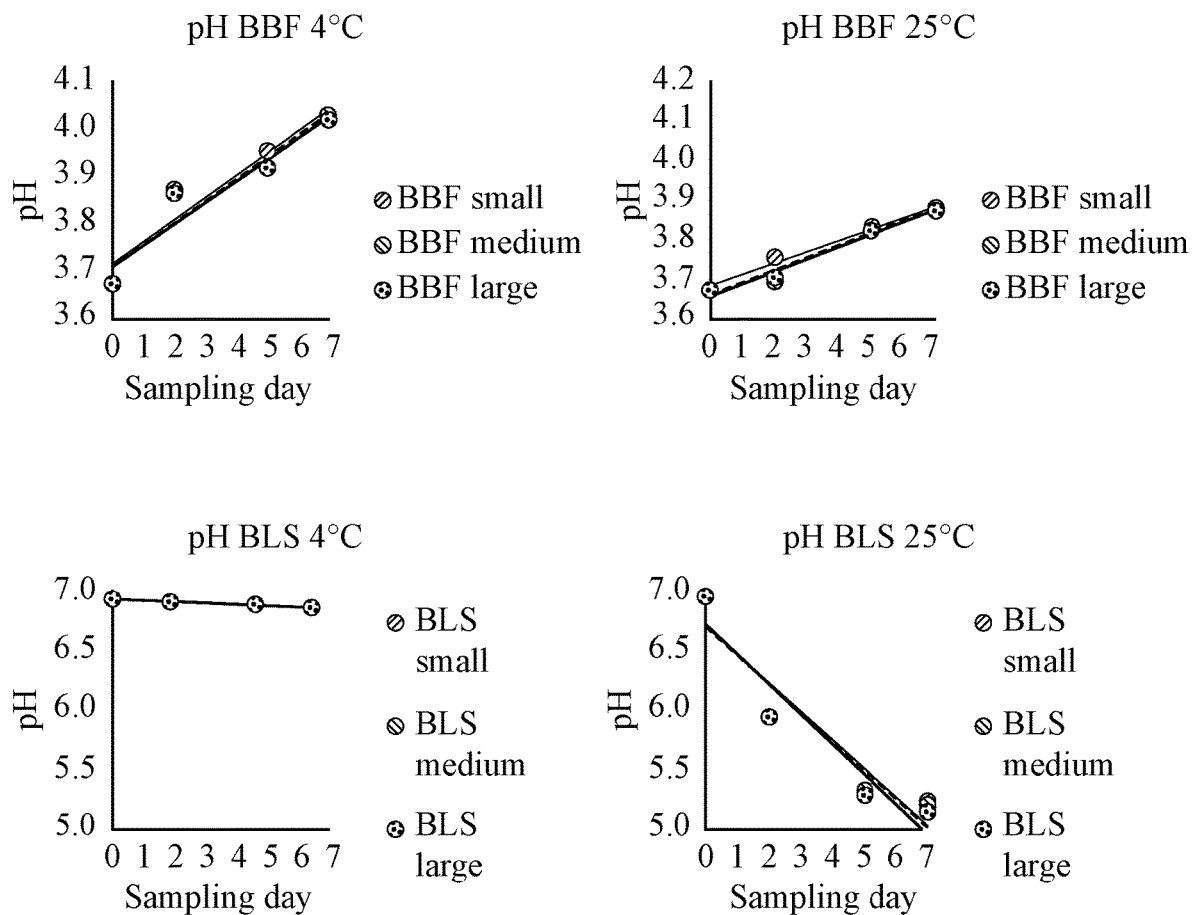
FIG. 14 BBF and BLS matrix pH with microorganisms incubated at 4° C. and 25° C.

In FIG. 14, the pH values for the BBF are presented at temperatures of 4° and 25° C. respectively, despite the cooling temperature the growth of the microorganism was very similar to the growth of the microorganism at room temperature (25° C.) and the similarity is also evident in the change of pH since for the samples at 4° C. the pH of the BBF changed from 3.7 to 4 while for the room temperature it changed from 3.7 to 3.9; from the beginning to the end of the test, despite the fact that the microorganism is a *Lactobacillus*, it has been reported that some populations are able to increase the medium pH to bring it to more optimal conditions for survival.

The pH values for the BLS are also presented, in which a marked difference is seen between the temperatures that are not seen in the BBF. For the refrigeration temperature, the product maintained a constant pH of 7 for all sizes and throughout the experiment, while for room temperature 25° C., the change was very marked, starting at 7 and ending in 5.5.

Figure 15:
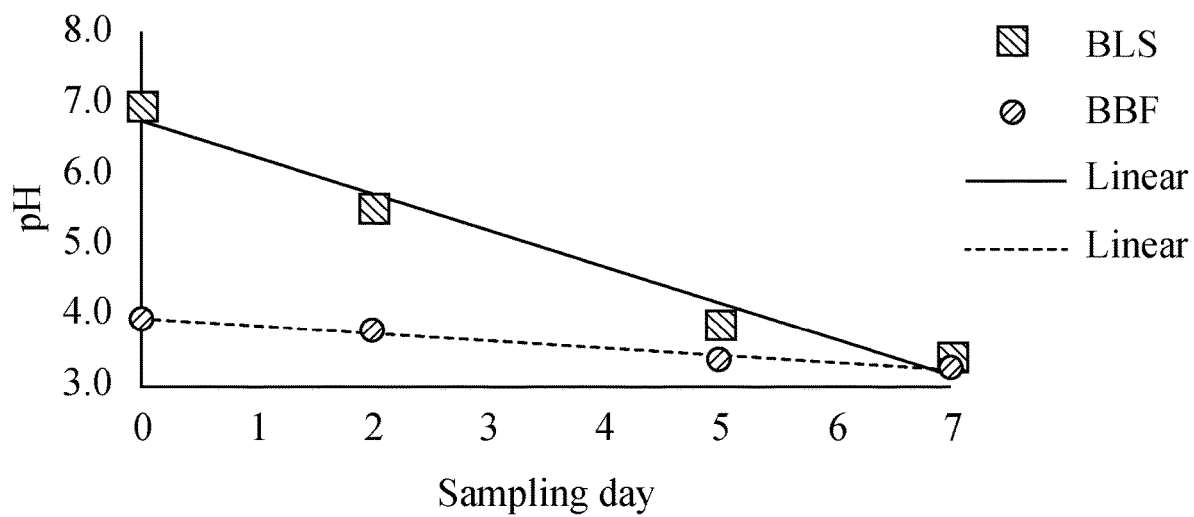
FIG. 15 BLS and BBF matrix pH with Lactospore® incubated at 25° C.

FIG. 15 shows the change in pH for the BBF and BLS matrices with sporulated microorganism; for BBF, a decrease in pH from 3.7 to 3.3 is observed and for BLS, an even greater decrease from 7 to 3.4. The changes observed in pH reflect the need for encapsulation due to undesirable physical-chemical effects in both dairy and non-dairy beverages.

Figure 16:
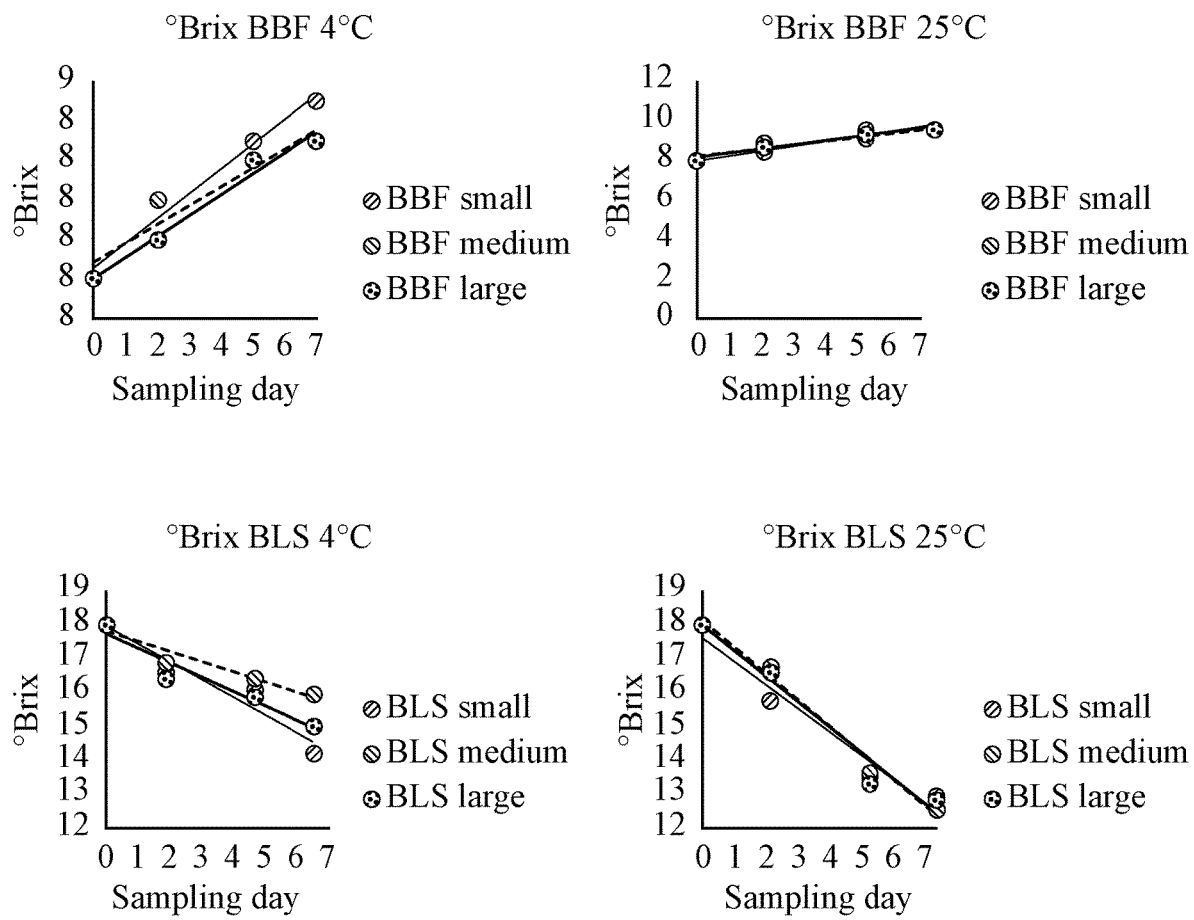
FIG. 16 BLS and BBF matrix °Brix incubated at 4° C. and 25° C.
Figure 17:
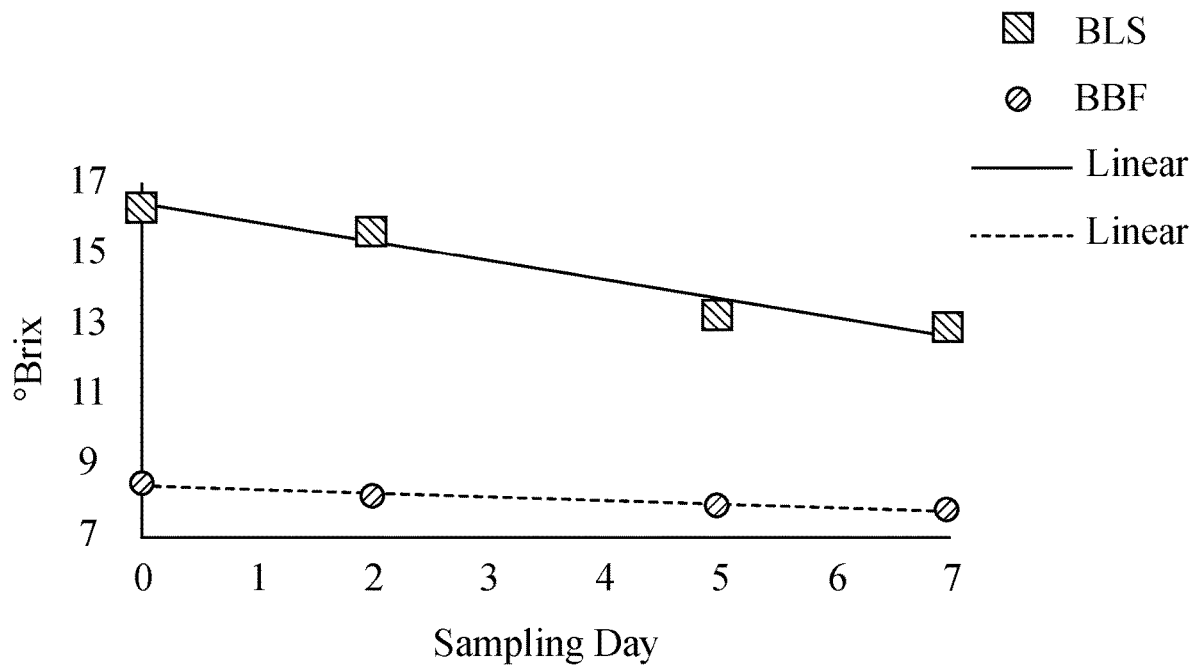
FIG. 17 BLS and BBF matrix °Brix incubated at 25° C.
Figure 18:
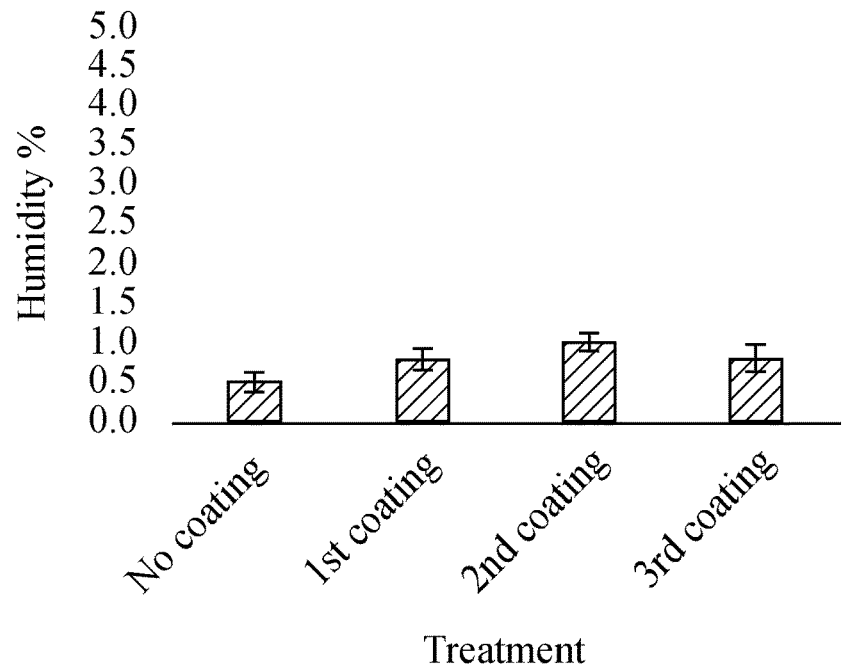
FIG. 18 Moisture percentage present in each treatment after fluidized bed.
Figure 18:
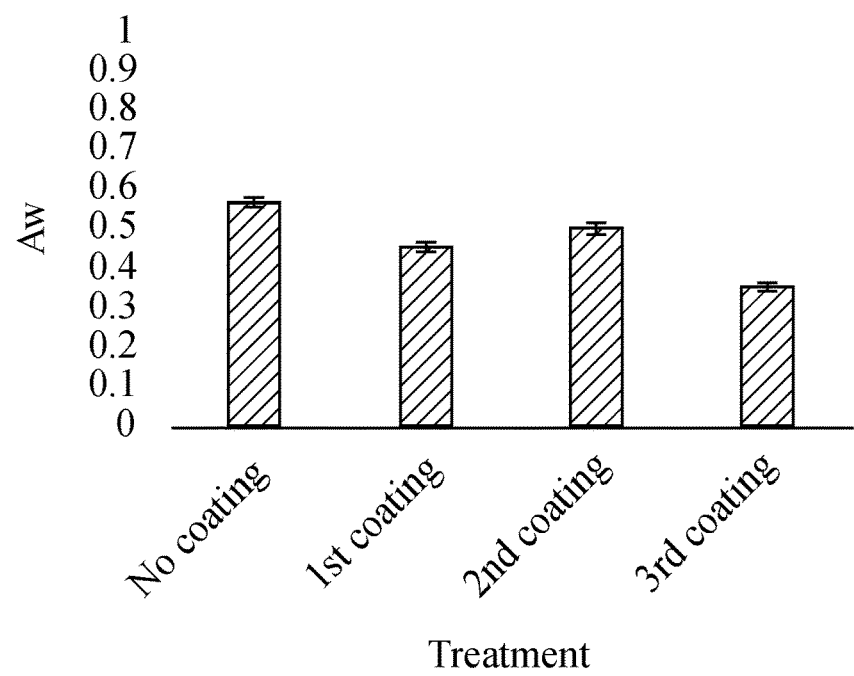

Regarding Brix degrees, FIG. 16 shows that the changes in the matrix are significant. However, FIG. 17 shows the importance of the microorganism encapsulation, since in matrices such as BLS, the change in °Brix is evident.

Example 8

Fluid Bed Coating

After performing the previous tests, it was decided to re-test the protein film coating by means of a fluid bed. However, for this test, wall materials selected for the commercial product BLS (fully hydrogenated palm oil) were used, which presented greater ease for hot spraying in the Spray Cooling equipment built at the university. The wax was melted at 70° C., mixed with the 1% sporulated microorganism and sprayed in the Spray Cooling equipment built at La Universidad de La Sabana. The coat was applied thereon in the HDB 15 Fluid Bed equipment (Bauer, Colombia) under the conditions reported in the previous experiment. The protein film was sprayed in a ratio of 400 g of protein film to 4000 g of lipid spheres of palm oil completely hydrogenated with sporulated microorganism, which is a proportion of 1:10. The protein film was the one selected in FIG. 3, as the one showing the highest reduction percentage in terms of diffusion.

During the coating procedure, three coating cycles were set with their respective drying and conditioning times at room temperature. Lipid spheres (i.e., samples of the uncoated product) were taken, after a first, second and third coating with a protein film for a total of four samples, which were tested for humidity, $a_w$ and diffusion in an aqueous medium. For this test, phosphate buffer was used as an aqueous medium to avoid erroneous counts due to possible microorganism growth in the medium.

FIG. 17 shows the humidity with which the different samples were obtained, all having very low humidity; below 1%, the same phenomenon that occurred for $a_w$. These values are favorable for the conservation and lengthening of shelf life for this type of product given the microorganism growth and the degradation by enzymatic reactions is inhibited.

Figure 19:
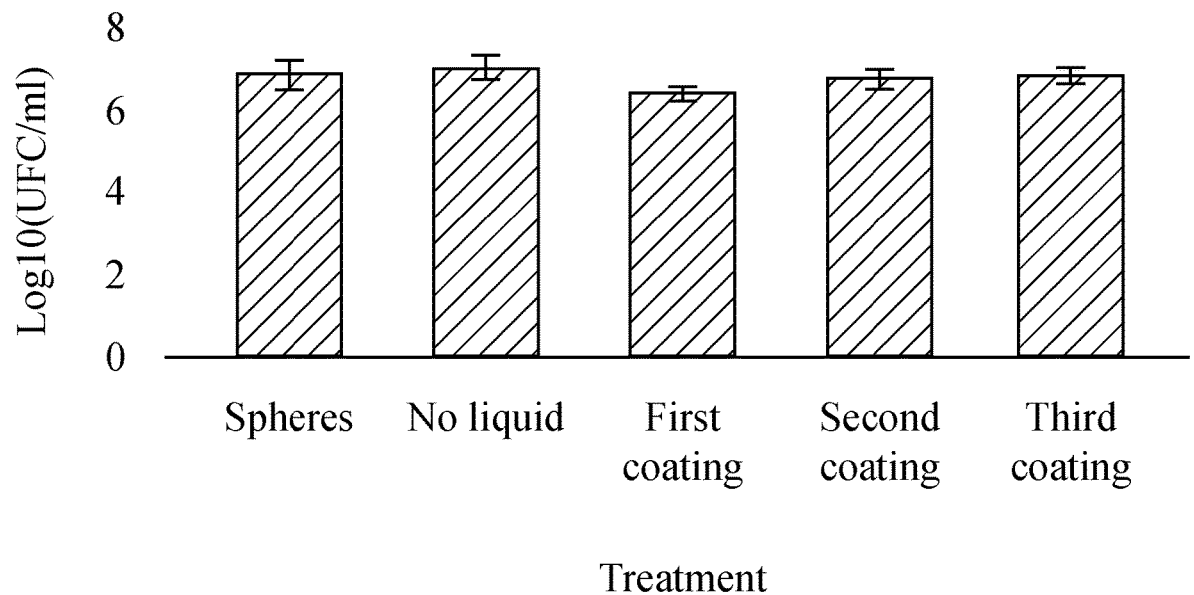
FIG. 19 Viable spore count in aqueous medium after each coating.
Figure 20:
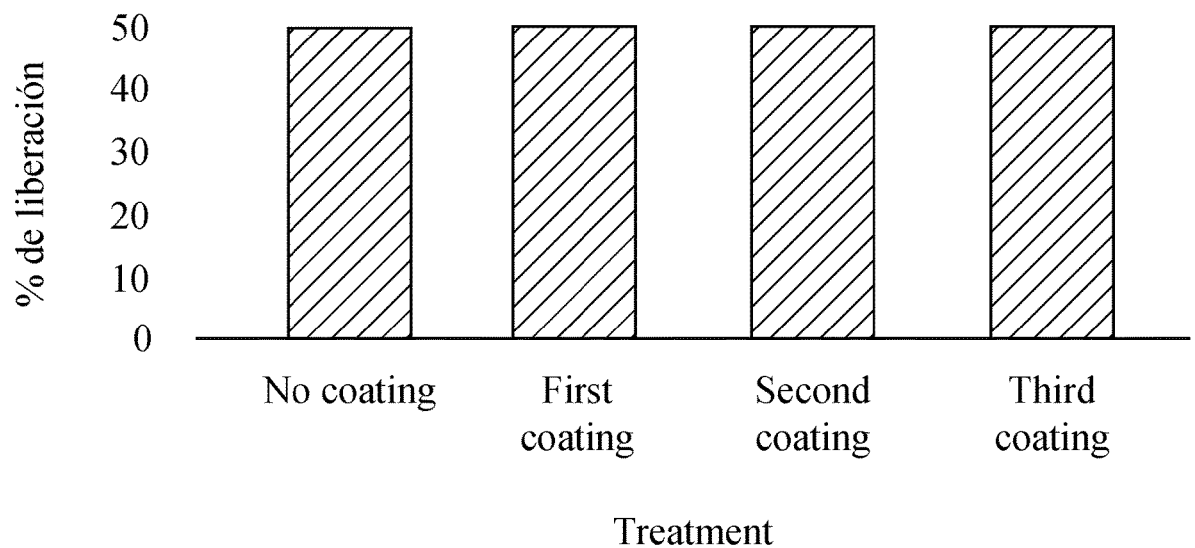
FIG. 20 Spore reduction percentage released in aqueous medium for each treatment.
Figure 21:
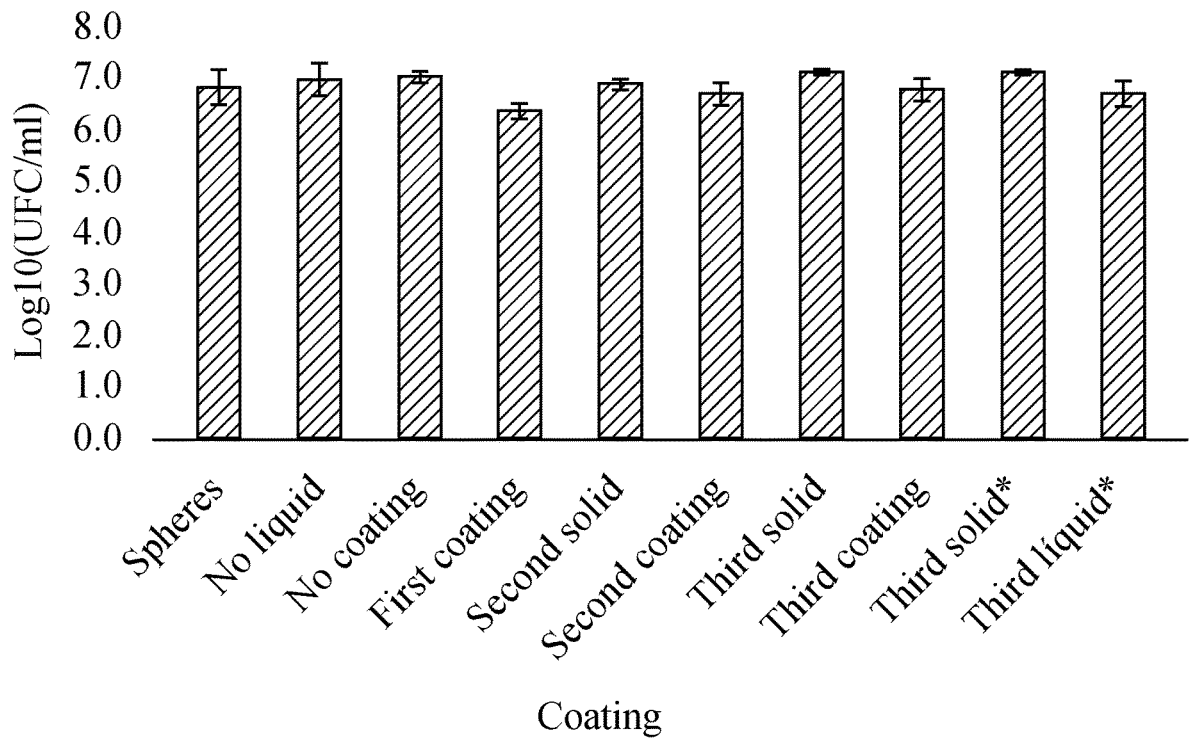
FIG. 21 Spore count for each coating layer (*Heat treatment was performed at 50° C. for 20 minutes).
Figure 22:
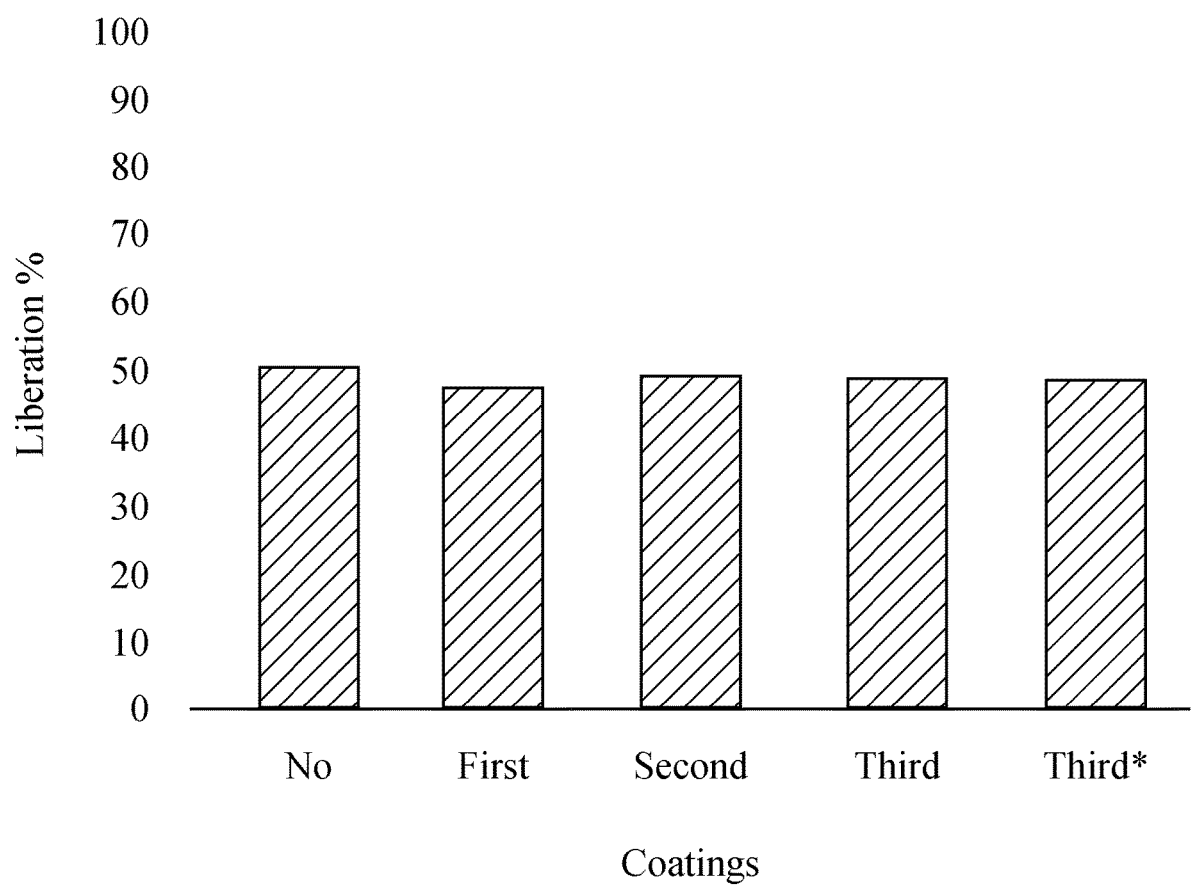
FIG. 22 Viable spore release percentage into an aqueous medium (*heat treatment at 50° C. for 20 minutes was performed).

FIG. 19 shows results corresponding to a phosphate buffer diffusion test based on the initial concentration of Lactospore® present in the uncoated lipid spheres (about 7 log units) to determine the diffusion of the other treatments. However, it was found that the diffusion in the medium was immediate (the release percentages for this test in each of the procedures exceeded 50% (FIG. 20)). For this reason, the test was repeated counting initial concentrations of the solid and liquid phase (FIG. 21 and FIG. 22). In these last two figures, the viability of the microcapsules in both the liquid and solid phases is shown. It is observed that the concentration in the solid and liquid phase for each of the tests was very similar; the release is almost immediate in each of the coatings, even for the uncoated ones. This is due to the fact that the coating possibly did not set uniformly around all the spheres leaving spaces through which microorganisms migrated easily.

The invention claimed is:

1. A probiotic microcapsule comprising a solid lipid sphere coated by a protein film:
    wherein the solid lipid sphere comprises between 0.1 and 3% of a sporulated probiotic; and between 97 and 99.9% of a lipid wall material, both based on the total weight of the solid lipid sphere;
    wherein the protein film comprises between 5 and 25% of a protein material; between 20 and 35% of a carbohydrate; and between 55 and 75% of water, based on the total weight of the protein film;
    wherein said sporulated probiotic is selected from the group consisting of *Bacillus coagulans, Bacillus subtilis, Bacillus clausii, Bacillus cereus, Bacillus licheniformis* and mixtures thereof;
    wherein said lipid wall material is selected from the group consisting of beeswax, palm kernel oil, palm oil, coconut oil, palm stearin, peanut butter, and mixtures thereof;
    wherein said protein material is selected from the group consisting of milk protein, whey, egg white, sodium caseinate, gelatin, and mixtures thereof.

2. The microcapsule of claim 1, wherein the carbohydrate is starch, which is selected from modified starch, pregelatinized starch, ungelatinized starch, native corn starch, modified corn starch, *yucca* starch, and mixtures thereof.

3. The microcapsule of claim 1, wherein the ratio protein film:solid lipid sphere is between 1:10 and 1:15.

4. The microcapsule of claim 1, wherein the protein film comprises between 5 and 12% of lyophilized egg white, between 5 and 13% of sodium caseinate, and between 45 and 75% of distilled water, based on the total weight of the protein film.

5. The microcapsule according to claim 1, wherein,
    the solid lipid sphere comprises 1% sporulated probiotic and 99% palm oil based on the total weight of the solid lipid sphere;
    the protein film comprises 5% egg albumin, 5% sodium caseinate, 25% modified corn starch, and 65% distilled water based on the total weight of the protein film; and
    wherein the protein film:solid lipid sphere ratio is 1:10.

6. The microcapsule of claim 1, wherein the microcapsule has a particle size between 400 and 1200 μm.

7. The microcapsule of claim 1, wherein the microcapsule does not need refrigeration.

8. A process for the encapsulation of probiotics comprising:
    a) mixing a sporulated probiotic with a melted or liquid-phase lipid wall material to obtain a solid lipid sphere;
    b) mixing a protein material, a carbohydrate and water until a protein film is formed;
    c) homogenizing the protein film; and
    d) fluidizing the solid lipid sphere of step (a), and spraying the protein film of step (c) on the solid lipid sphere,
    wherein the solid lipid sphere comprises between 0.1 and 3% of a sporulated probiotic; and between 97 and 99.9% of a lipid wall material, both based on the total weight of the solid lipid sphere;
    wherein the protein film comprises between 5 and 25% of a protein material; between 20 and 35% of a carbohydrate; and between 55 and 75% of water, based on the total weight of the protein film;
    wherein said sporulated probiotic is selected from the group consisting of *Bacillus coagulans, Bacillus subtilis, Bacillus clausii, Bacillus cereus, Bacillus licheniformis* and mixtures thereof;
    wherein said lipid wall material is selected from the group consisting of beeswax, palm kernel oil, palm oil, coconut oil, palm stearin, peanut butter, and mixtures thereof;
    wherein said protein material is selected from the group consisting of milk protein, whey, egg white, sodium caseinate, gelatin, and mixtures thereof.

9. The process of claim 8, wherein the mixing in step (b) is performed with stirring between 500 and 5000 rpm.

10. The process of claim 8, wherein the homogenization in step (c) is carried out at a pressure greater than 10,000 psi.

11. The process of claim 8, wherein the homogenization in step (c) is performed by means of micro-fluidization.

12. The process of claim 8, wherein the fluidization in step (d) is performed by atomization at a temperature ranging between 40° and 60° C., and between 20 min and 40 min.

13. The microcapsule of claim 1, wherein the egg white comprises egg albumin.

14. The microcapsule of claim 1, wherein the whey comprises whey protein.

15. The microcapsule of claim 1, wherein the protein film further comprises lecithin and polysorbates.

* * * * *